(12) United States Patent
Peyman et al.

(10) Patent No.: US 6,747,148 B2
(45) Date of Patent: Jun. 8, 2004

(54) SULFONAMIDE DERIVATIVES AS INHIBITORS OF BONE RESORPTION AND AS INHIBITORS OF CELL ADHESION

(75) Inventors: Anuschirwan Peyman, Kelkheim (DE); David William Will, Schwalbach (DE); Jochen Knolle, Kriftel (DE); Karlheinz Scheunemann, Liederbach (DE); Denis Carniato, Marcoussis (FR); Jean-Francois Gourvest, Souilly (FR); Thomas R. Gadek, Oakland, CA (US); Robert McDowell, San Francisco, CA (US); Sarah Catherine Bodary, San Bruno, CA (US); Robert Andrew Cuthbertson, Victoria (AU)

(73) Assignees: Hoechst Marion Roussel Deutschland GmbH, Frankfurt (DE); Genentech, Inc., South San Francisco, CA (US)

( * ) Notice: Subject to any disclaimer, the term of this patent is extended or adjusted under 35 U.S.C. 154(b) by 21 days.

(21) Appl. No.: 09/972,190

(22) Filed: Oct. 9, 2001

(65) Prior Publication Data

US 2002/0065271 A1 May 30, 2002

Related U.S. Application Data

(62) Division of application No. 09/564,988, filed on May 5, 2000, now Pat. No. 6,313,119, which is a continuation of application No. 09/235,271, filed on Jan. 22, 1999, now abandoned.
(60) Provisional application No. 60/072,313, filed on Jan. 23, 1998.

(51) Int. Cl.$^7$ .................... C07C 211/119; C07D 239/26
(52) U.S. Cl. ................. 544/122; 544/159; 546/222; 546/300; 548/334.1; 560/10; 560/13; 562/427; 562/430
(58) Field of Search ............. 560/10, 13; 562/427, 562/430; 544/122, 159; 546/222, 300; 548/334.1

(56) References Cited

U.S. PATENT DOCUMENTS

| 5,707,994 A | 1/1998 | Ikeda et al. ................. 514/255 |
| 6,017,925 A | 1/2000 | Duggan ........................ 514/300 |
| 6,313,119 B1 * | 11/2001 | Peyman et al. ........... 514/235.8 |

FOREIGN PATENT DOCUMENTS

| EP | 0 528 586 | 2/1993 |
| EP | 0 528 587 | 2/1993 |
| EP | 0 820 991 | 1/1998 |
| EP | 0 933 367 | 8/1999 |
| WO | 94/08577 | 4/1994 |
| WO | 94/12181 | 6/1994 |
| WO | 95/32710 | 12/1995 |
| WO | 96/00574 | 1/1996 |
| WO | 96/00730 | 1/1996 |
| WO | 97/21726 | 6/1997 |
| WO | 98/00395 | 1/1998 |
| WO | 98/31359 | 7/1998 |

OTHER PUBLICATIONS

Jardine, Paul Da Silva et al., "Anti–Osteoporosis Agents", *Annual Reports in Medicinal Chemistry* (31) Chapter 22, pp. 211–220, (1996).

Horton, M.A. et al., "Arg–Gly–Asp (RGD) Peptides and the Anti–Vitronectin Receptor Antibody 23C6 Inhibit Dentine Resorption and Cell Spreading by Osteoclasts", *Experimental Cell Research*, pp. 368–375, (1991).

Sato M. et al., "Echistatin is a Potent Inhibitor of Bone Resorption in Culture", *The Journal of Cell Biology*, 111, pp. 1713–1723, (Oct. 1990).

Fisher, John E et al., Inhibition of Osteoclastic Bone Resorption in Vivo by Echistatin, an Arginyl–Glycyl–Aspartyl (RGD)–Containing Protein, *Endocrinology*, (132)3, pp. 1411–1413, (1993).

Brown, Steven L. et al., "Stimulation of migration of human aortic smooth muscle cells by vitronectin implications for atherosclerosis", *Cardiovascular Research* (28), pp. 1815–1820, (1994).

Brooks, Peter C. et al., *Integrin $\alpha_v\beta_3$ Antagonists Promote Tumor Regression by Inducing Apoptosis of Angiogenic Blood Vessels*, *Cell* (79), pp. 1157–1164, (Dec. 1994).

Engleman, V. Wayne et al., "Cell Adhesion Integrin as Pharmaceutical Targets", *Annual Reports in Medicinal Chemistry*, (31) Chapter 20, pp. 191–200, (1996).

Stracke, Mary L. et al., "Tumor Cell Motility and Invasion", *Encyclopedia of Cancer* (vol. III), pp. 1855–1867, (1997).

Hillis, Graham S., et al., "Integrins and disease", *Clinical Science* (91), pp. 639–650, (1996).

Carron, Christopher P. et al., "A Peptidomimetic Antagonist of the Integrin $\alpha_v\beta_3$ Inhibits Leydig Cell Tumor Growth and the Development of Hypercalcemia of Malignancy", *Cancer Research* (58), pp. 1930–1935, (5/98).

Friedlander, Martin et al., "Defintion of Two Angiogenic Pathways by Distinct $\alpha_v$ Integrins", *Science*, (270) pp. 1500–1502, (Dec. 1995).

(List continued on next page.)

*Primary Examiner*—Richard L. Raymond
(74) *Attorney, Agent, or Firm*—Foley & Lardner LLP

(57) ABSTRACT

Sulfonamide derivatives, their physiologically tolerable salts and their prodrugs according to the present invention are vitronectin receptor antagonists and inhibitors of cell adhesion, as well as inhibit bone resorption by osteoclasts. These derivatives, salts and prodrugs are pharmaceutically active compounds useful in the therapy and prophylaxis of diseases which are caused at least partially by an undesired extent of bone resorption, for example of osteoporosis. Processes for the preparation of the sulfonamide derivatives according to the present invention, the use of these derivatives as pharmaceutically active ingredients, and pharmaceutical preparations comprising these derivatives also are disclosed.

6 Claims, No Drawings

OTHER PUBLICATIONS

Fleisher, David et al., "Improved oral drug delivery: solubility limitations overcome by the use of prodrugs" *Advanced Drug Reviews* (19), pp. 115–130, (1996), Elsevier, Paris.

Bundgaard, Hans, Novel chemical approaches in prodrug design, *Drugs of the Future* (16)5, pp. 443–458, (1991).

Saulnier, Mark G. et al., "An Efficient Method for the Synthesis of Guanidino Prodrugs", *Bioorganic & Medical Chemistry Letters* (4)16, pp. 1985–1990, (1994).

Safadi, Muhammad et al., "Phosphoryloxymethyl Carbamates and Carbonates—Novel Water Soluble Prodrugs for Amines and Hindered Alcohols", *Pharmaceutical Research* (10)9, pp. 1350–1355, (1993).

König, W. et al., "Perchloric acid in peptide chemistry," *Peptides* pp. 143–145, (1990).

Staab, H.A., "Synthesis Using Heterocyclic Amids (Azolides)", *Angew, Chem. Internat. Edit.* (1)7, pp. 351–367, (1962).

Yatohgo, Takemi et al., Novel Purification of Vitronectin from Human Plasma by Heparin Affinity Chromatography, *Cell Structure and Function* 13, pp. 281–292, (1988).

Storgard, Chris M. et al., (103)1, Decreased angiogenesis and arthritic disease in rabbits treated with An $\alpha_v\beta_3$ antagonist, *The Journal of Clinical Investigation* (103)1, pp. 47–54, (Jan. 1999).

Yue, Tian–Li et al., "SK&F107260, a Cyclic RGD Peptide, Inhibits Integrin $\alpha_v\beta_3$–Mdiated Vascular Smooth Muscle Cell Migration, in vitro, and Reduces Neointima Formation Following Balloon Injury to the Rat Carotid Artery, in vivo,", *Pharmacology Review and Communications*, (100)9, pp. 9–18, (1998).

Yamamoto, Michiko et al., "The Integrin Ligand Echistatin Prevents Bone Loss in Ovariectomized Mice and Rats", *Endocrinology*,(139)3, pp. 1411–1419, (1998).

* cited by examiner

SULFONAMIDE DERIVATIVES AS INHIBITORS OF BONE RESORPTION AND AS INHIBITORS OF CELL ADHESION

INFORMATION ON RELATED APPLICATIONS

This application is a divisional of Ser. No. 09/564,988, filed May 5, 2000, now U.S. Pat. No. 6,313,119, which is a continuation of Ser. No. 09/235,271, filed Jan. 22, 1999, now abandoned, which claims priority to 60/072,313 filed Jan. 23, 1998.

BACKGROUND OF THE INVENTION

Human bones are subject to a constant, dynamic renovation process comprising bone resorption and bone formation. These processes are controlled by types of cells specialized for these purposes. Bone resorption is based on the destruction of bone matrix by osteoclasts. The majority of bone disorders are based on a disturbed equilibrium between bone formation and bone resorption. Osteoporosis is a disease characterized by low bone mass and enhanced bone fragility resulting in an increased risk of fractures. It results from a deficit in new bone formation versus bone resorption during the ongoing remodelling process. Conventional osteoporosis treatment includes, for example, the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (Jardine et al, Annual Reports in Medicinal Chemistry 31: 211 (1996)).

Activated osteoclasts are polynuclear cells having a diameter of up to 400 µm, which remove bone matrix. Activated osteoclasts become attached to the surface of the bone matrix and secrete proteolytic enzymes and acids into the so-called "sealing zone," the region between their cell membrane and the bone matrix. The acidic environment and the proteases cause the destruction of the bone.

Studies have shown that the attachment of osteoclasts to the bones is controlled by integrin receptors on the cell surface of osteoclasts. Integrins are a superfamily of receptors which include, inter alia, the fibrinogen receptor $\alpha_{IIb}\beta_3$ on the blood platelets and the vitronectin receptor $\alpha_v\beta_3$. The vitronectin receptor $\alpha_v\beta_3$ is a membrane glycoprotein which is expressed on the cell surface of a number of cells such as endothelial cells, cells of the vascular smooth musculature, osteoclasts and tumor cells. The vitronectin receptor $\alpha_v\beta_3$, which is expressed on the osteoclast membrane, controls the process of attachment to the bones and bone resorption and thus contributes to osteoporosis. $\alpha_v\beta_3$ in this case binds to bone matrix proteins such as osteopontin, bone sialoprotein and thrombospontin, which contain the tripeptide motif Arg-Gly-Asp (or RGD).

Horton and coworkers describe RGD peptides and an anti-vitronectin receptor antibody (23C6) which inhibit tooth destruction by osteoclasts and the migration of osteoclasts (Horton et al, Exp. Cell. Res. 195: 368(1991)). In J. Cell Biol. 111: 1713 (1990), Sato et al describe echistatin, an RGD peptide from snake venom, as a potent inhibitor of bone resorption in a tissue culture and as an inhibitor of osteoclast adhesion to the bones. Fischer et al (Endocrinology 132: 1411 (1993)) were able to show in the rat that echistatin also inhibits bone resorption in vivo.

It was furthermore shown that the vitronectin $\alpha_v\beta_3$ on human cells of the vascular smooth musculature of the aorta stimulates the migration of these cells into the neointima, which finally leads to arteriosclerosis and restenosis after angioplasty (Brown et al. Cardiovascular Res. 28: 1815 (1994)).

Brooks et al., Cell 79: 1157 (1994), showed that antibodies against $\alpha_v\beta_3$ or $\alpha_v\beta_3$ antagonists can cause a shrinkage of tumors by inducing the apoptosis of blood vessel cells during angiogenesis. The vitronectin receptor $\alpha_v\beta_3$ is also involved in the progression of a variety of other types of cancer, and is overexpressed in malignant melanoma cells (Engleman et al, Annual Reports in Medicinal Chemistry 31: 191 (1996)). The melanoma invasiveness correlated with this overexpression (Stracke et al, Encylopedia of Cancer, Volume III, 1855, Academic Press (1997); Hillis et al., Clinical Science 91: 639 (1996)). Carron et al., Cancer Res. 58: 1930 (1998), describe the inhibition of tumor growth and the inhibition of hypercalcemia of malignancy using an $\alpha_v\beta_3$ antagonist.

Cheresh et al., Science 270: 1500 (1995), describe anti-$\alpha_v\beta_3$ antibodies or $\alpha_v\beta_3$ antagonists which inhibit the bFGF-induced angiogenesis processes in the rat eye, a property which can be used therapeutically in the treatment of retinopathies.

Thus, vitronectin receptors, and the interactions in which they are involved, are involved in a number of diseases. Influencing of the vitronectin receptor or of the interactions in which it is involved thus offers the possibility of influencing numerous disease states for whose therapy and prophylaxis there continues to be a need for suitable pharmaceutical active ingredients.

WO-A-94/12181 describes substituted aromatic or non-aromatic ring systems, and WO-A-94/08577 describes substituted heterocycles as fibrinogen receptor antagonists and inhibitors of platelet aggregation. EP-A-528586 and EP-A-528587 disclose aminoalkyl-substituted or heterocyclyl-substituted phenylalanine derivatives, and WO-A-95/32710 discloses aryl derivatives as inhibitors of bone resorption by osteoclasts. WO-A-96/00574 describes benzodiazepines, and WO-A-96/00730 describes fibrinogen receptor antagonist templates, in particular benzodiazepines which are linked to a nitrogen-bearing 5-membered ring, as vitronectin receptor antagonists. WO-A-98/00395 (DE-A-19654483) describes vitronectin receptor antagonists derived from a tyrosine scaffold. EP-A-820991 (German patent application 19629816.4) describes cycloalkyl derivatives and European patent application 97122520.6 describes carbamic ester derivatives which are vitronectin receptor antagonists. There remains, however, the need for additional compounds that influence the vitronectin receptor and/or the interactions in which it is involved.

In accordance with this need, the present inventors have discovered that certain sulfonamide derivatives are particularly strong inhibitors of the vitronectin receptor and of bone resorption by osteoclasts.

SUMMARY OF THE INVENTION

The present invention relates to sulfonamide derivatives, their physiologically tolerable salts and their prodrugs. In accordance with one aspect of the invention, there are provided compounds having the general formula I:

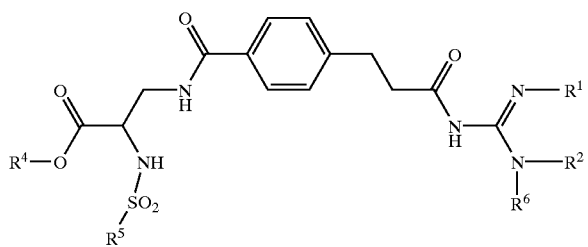

wherein:

R¹ and R² independently of one another are hydrogen or (C₁-C₆)-alkyl which is unsubstituted or substituted by R³, or in which the radicals R¹— and R²— together are a saturated or unsaturated bivalent (C₂-C₉)-alkylene radical which is unsubstituted or is substituted by one or more groups from the group consisting of halogen, (C₁-C₆)-alkyl, (C₁-C₆)-alkoxy, (C₆-C₁₄)-aryl, (C₆-C₁₄)-aryl-(C₁-C₆)-alkyl-, (C₅-C₁₄)-heteroaryl, (C₅-C₁₄)-heteroaryl-(C₁-C₆)-alkyl-, (C₃-C₁₂)-cycloalkyl, (C₃-C₁₂)-cycloalkyl-(C₁-C₆)-alkyl- and oxo, where a 5-membered to 7-membered saturated or unsaturated ring which is unsubstituted or is substituted by R³ and which is a carbocyclic ring or a heterocyclic ring containing one or two ring nitrogen atoms, can be fused to a carbon-carbon bond in the (C₂-C₉)-alkylene radical;

R³ is (C₁-C₁₀)-alkyl, (C₃-C₂₀)-monocycloalkyl, (C₅-C₂₀)-bicycloalkyl, (C₅-C₂₀)-tricycloalkyl, (C₁-C₈)-alkoxy, (C₆-C₁₄)-aryl, (C₆-C₁₄)-aryl-(C₁-C₄)-alkyl-, (C₅-C₁₄)-heteroaryl, (C₅-C₁₄)-heteroaryl-(C₁-C₄)-alkyl-, halogen, trifluoromethyl, cyano, hydroxyl, oxo, nitro, amino, —NH—(C₁-C₄)-alkyl, —N((C₁-C₄)-alkyl)₂, —NH—CO—(C₁-C₄)-alkyl, or —CO—(C₁-C₄)-alkyl;

R⁴ is hydrogen, (C₁-C₆)-alkyl-CO—O—(C₁-C₄)-alkyl- or (C₁-C₆)-alkyl which is unsubstituted or is substituted by a radical selected from the group consisting of hydroxyl, (C₁-C₄)-alkoxy, (C₁-C₄)-alkyl-S(O)₂—, —NR⁷R⁷'' and —N⁺R⁷R⁷'R⁷''Q⁻, where R⁷, R⁷' and R⁷'' independently of one another are hydrogen, (C₁-C₆)-alkyl, (C₅-C₁₄)-aryl or (C₅-C₁₄)-aryl-(C₁-C₆)-alkyl- and Q⁻ is a physiologically tolerable anion, or in which R⁴ is one of the radicals

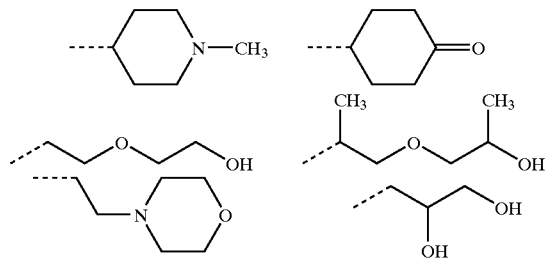

in which the bonds, via which the radicals are bonded, are indicated by dashed lines;

R⁵ is (C₁-C₂₀)-alkyl, (C₃-C₂₀)-monocycloalkyl, (C₅-C₂₀)-bicycloalkyl, (C₅-C₂₀)-tricycloalkyl, (C₆-C₁₄)-aryl, (C₅-C₁₄)-heteroaryl, (C₆-C₁₄)-aryl-(C₁-C₆)-alkyl- or (C₅-C₁₄)-heteroaryl-(C₁-C₆)-alkyl-, wherein one or more carbon atoms of the alkyl radical, the monocycloalkyl radical, the bicycloalkyl radical and the tricycloalkyl radical is optionally replaced by identical or different atoms selected from the group consisting of nitrogen, oxygen and sulfur, and wherein the aryl radical, the heteroaryl radical, the alkyl radical, the monocycloalkyl radical, the bicycloalkyl radical and the tricycloalkyl radical each is unsubstituted or is substituted by one, two or three radicals R³; and R⁶ is hydrogen, (C₁-C₆)-alkyl-O—CO—, hydroxyl, (C₁-C₆)-alkyl-O—CO—O— or nitro;

in all their stereoisomeric forms and mixtures thereof in all ratios, and their physiologically tolerable salts and their prodrugs.

In accordance with another aspect of the invention, there is provided a process for the preparation of foregoing compounds comprising linking two or more fragments which can be derived retrosynthetically from the compound of formula I. In one embodiment, this process comprises reacting a carboxylic acid or a carboxylic acid derivative of formula II,

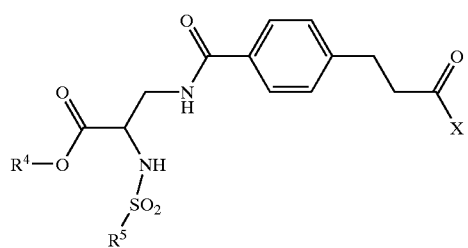

wherein R⁴ and R⁵ are defined as above, or alternatively functional groups are present in the form of precursors or in protected form, and X is a nucleophilically substitutable leaving group;

with a guanidine or guanidine derivative of the formula III,

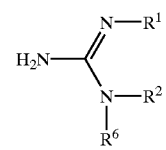

wherein R¹, R² and R⁶ are defined as above, or alternatively functional groups are present in the form of precursors or in protected form.

In accordance with yet another aspect of the invention, there are provided pharmaceutical compositions comprising at least one of the compounds of the present invention and a pharmaceutically innocuous carrier.

In accordance with still another aspect of the present invention, there are provided methods for treating or preventing a disease characterized by or influenced by an interaction between a vitronectin receptor and a ligand in cell-cell interaction processes or cell-matrix interaction processes comprising administering a compound of the present invention. In one embodiment, there is method of inhibiting bone resorption comprising administering a compound of the present invention. In another embodiment, a method of treating or preventing osteoporosis, hypercalcemia, or osteopenia comprising administering a compound of the present invention is provided. In still another embodiment, a method of inhibiting tumor growth or metastasis comprising administering a compound of the present invention is provided. In yet another embodiment, a method of treating or preventing inflammation, cardiovascular disorders, restenosis, arteriosclerosis, nephropathies or retinopathies comprising administering a compound of the present invention is provided.

DETAILED DESCRIPTION OF THE INVENTION

The present invention relates to sulfonamide derivatives, their physiologically tolerable salts and their prodrugs.

These sulfonamide derivatives are valuable pharmaceutically active compounds. In particular, they are vitronectin receptor antagonists and inhibitors of cell adhesion. They also inhibit bone resorption by osteoclasts. The sulfonamide derivatives of the present invention are suitable, for example, for the therapy and prophylaxis of diseases which are caused at least partially by an undesired extent of bone resorption, for example of osteoporosis. The present invention furthermore relates to processes for the preparation of the sulfonamide derivatives according to the present invention, the use of these derivatives as pharmaceutically active ingredients, and pharmaceutical preparations comprising these derivatives.

The sulfonamide derivatives of the present invention may be represented by the following general formula I:

I

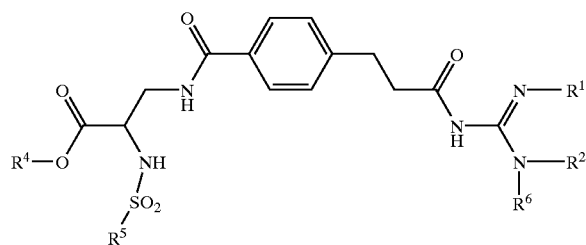

in which:

$R^1$ and $R^2$ independently of one another are hydrogen or $(C_1-C_6)$-alkyl which is unsubstituted or substituted by $R^3$, or in which the radicals $R^1$— and $R^2$— together are a saturated or unsaturated bivalent $(C_2-C_9)$-alkylene radical, for example the group —$(CH_2)_p$—, in which p is 2, 3, 4, 5, 6, 7, 8 or 9, which is unsubstituted or is substituted by one or more groups from the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$-alkyl- and oxo, where a 5-membered to 7-membered saturated or unsaturated ring which is unsubstituted or is substituted by $R^3$, in particular by one or two radicals $R^3$, and which is a carbocyclic ring or a heterocyclic ring containing one or two ring nitrogen atoms, can be fused to a carbon-carbon bond in the $(C_2-C_9)$-alkylene radical;

$R^3$ is $(C_1-C_{10})$-alkyl, $(C_3-C_{20})$-monocycloalkyl, $(C_5-C_{20})$-bicycloalkyl, $(C_5-C_{20})$-tricycloalkyl, $(C_1-C_8)$-alkoxy, $(C_6-C_{14})$-aryl, $(C_6-C_{14})$-aryl-$(C_1-C_4)$-alkyl-, $(C_5-C_{14})$-heteroaryl, $(C_5-C_{14})$-heteroaryl-$(C_1-C_4)$-alkyl-, halogen, trifluoromethyl, cyano, hydroxyl, oxo, nitro, amino, —NH—$(C_1-C_4)$-alkyl, —N(($C_1-C_4$)-alkyl)$_2$, —NH—CO—$(C_1-C_4)$-alkyl, or —CO—$(C_1-C_4)$-alkyl;

$R^4$ is hydrogen, $(C_1-C_6)$-alkyl-CO—O—$(C_1-C_4)$-alkyl- or $(C_1-C_6)$-alkyl which is unsubstituted or is substituted by a radical from the group consisting of hydroxyl, $(C_1-C_4)$-alkoxy, $(C_1-C_4)$-alkyl-$S(O)_2$—, —$NR^7R^{7'}$ and —$N^+R^7R^{7'}R^{7''}Q^-$, where $R^7$, $R^{7'}$ and $R^{7''}$ independently of one another are hydrogen, $(C_1-C_6)$-alkyl, $(C_5-C_{14})$-aryl or $(C_5-C_{14})$-aryl-$(C_1-C_6)$-alkyl- and $Q^-$ is a physiologically tolerable anion, or in which $R^4$ is one of the radicals:

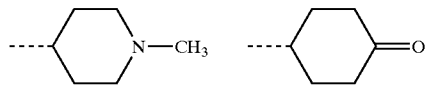

-continued

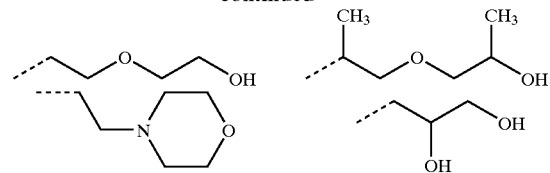

in which the bonds, via which the radicals are bonded, are indicated by dashed lines;

$R^5$ is $(C_1-C_{20})$-alkyl, $(C_3-C_{20})$-monocycloalkyl, $(C_1-C_{20})$-bicycloalkyl, $(C_5-C_{20})$-tricycloalkyl, $(C_6-C_{14})$-aryl, $(C_5-C_{14})$-heteroaryl, $(C_6-C_{14})$-aryl-$(C_1-C_6)$-alkyl- or $(C_5-C_{14})$-heteroaryl-$(C_1-C_6)$-alkyl-, wherein one or more carbon atoms, in particular one, two, three, or four carbon atoms, of the alkyl radical, the monocycloalkyl radical, the bicycloalkyl radical and the tricycloalkyl radical may be replaced by identical or different atoms selected from the group consisting of nitrogen, oxygen and sulfur, and wherein the aryl radical, the heteroaryl radical, the alkyl radical, the monocycloalkyl radical, the bicycloalkyl radical and the tricycloalkyl radical each is unsubstituted or is substituted by one, two or three radicals $R^3$;

$R^6$ is hydrogen, $(C_1-C_6)$-alkyl-O—CO—, hydroxyl, $(C_1-C_6)$-alkyl-O—CO—O— or nitro;

in all their stereoisomeric forms and mixtures thereof in all ratios, and their physiologically tolerable salts and their prodrugs.

All radicals which can occur several times in the compounds of the formula I, for example the radicals $R^3$, can each independently of one another have the meanings indicated, and can in each case be identical or different. Radicals which independently of one another can have a meaning indicated, can in each case be identical or different.

Alkyl radicals can be straight-chain or branched and can be saturated or monounsaturated or polyunsaturated. This also applies if they carry substituents or occur as substituents of other radicals, for example in alkoxy radicals, alkoxycarbonyl radicals or arylalkyl radicals. The same applies to alkylene radicals (=bivalent alkyl radicals=saturated or unsaturated alkanediyl radicals). Examples of suitable alkyl radicals containing from 1 to 20 carbon atoms are methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these radicals, isopropyl, isobutyl, isopentyl, neopentyl, isohexyl, isodecyl, 3-methylpentyl, 2,3,4-trimethylhexyl, sec-butyl, tert-butyl, tert-pentyl. A preferred group of alkyl radicals is formed by the radicals methyl, ethyl, n-propyl, isopropyl, n-butyl, isobutyl, sec-butyl and tert-butyl. The bivalent radicals corresponding to the abovementioned monovalent radicals, for example methylene, 1,1-ethylene (=methylmethylene), 1,2-ethylene, 1,3-propylene, 1,2-propylene (=1-methylethylene and 2-methylethylene), 2,3-butylene (=1,2-dimethyl-1,2-ethylene), 1,4-butylene, 1,6-hexylene, are examples of alkylene radicals.

Unsaturated alkyl radicals are, for example, alkenyl radicals such as vinyl, 1-propenyl, allyl, butenyl, 3-methyl-2-butenyl, or alkynyl radicals such as ethynyl, 1-propynyl or propargyl. Unsaturated alkylene radicals, i.e. alkenylene and alkynylene radicals (=alkenediyl and alkynediyl radicals), can likewise be straight-chain or branched. Examples of alkenylene radicals are vinylene or propenylene, and examples of alkynylene radicals are ethynylene or propynylene. Alkyl radicals can also be unsaturated when they are substituted. An example of an arylalkyl radical unsaturated in the alkyl moiety is styryl (=2-phenylethenyl).

Unless specified otherwise, cycloalkyl radicals can be monocyclic, bicyclic or tricyclic, i.e. they can be monocycloalkyl radicals, bicycloalkyl radicals and tricycloalkyl radical, provided they have a suitable number of carbon atoms. Monocycloalkyl radicals are, for example, cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclooctadecyl which, can also be substituted by, for example, $(C_1-C_4)$-alkyl. Examples of substituted cycloalkyl radicals which may be mentioned are 4-methylcyclohexyl and 2,3-dimethylcyclopentyl.

Bicycloalkyl radicals and tricycloalkyl radicals can be unsubstituted or substituted in any desired suitable position, for example by one or more oxo groups and/or one or more identical or different $(C_1-C_4)$-alkyl groups, for example methyl or isopropyl groups, preferably methyl groups. The free bond via which the bicyclic or the tricyclic radical is bonded can be located in any desired position in the molecule; the radical can thus be bonded via a bridgehead atom or an atom in a bridge. The free bond can also be located in any desired stereochemical position, for example in an exo-position or an endo-position. Examples of bicycloalkyl radicals and tricycloalkyl radicals are, camphanyl, bornyl, adamantyl, such as 1-adamantyl and 2-adamantyl, caranyl, epiisobornyl, epibornyl, norbornyl and norpinanyl.

Halogen is, for example, fluorine, chlorine, bromine or iodine.

$(C_5-C_{14})$-Aryl includes heterocyclic $(C_5-C_{14})$-aryl radicals (=$(C_5-C_{14})$-heteroaryl radicals) in which one or more of the 5 to 14 ring carbon atoms are replaced by heteroatoms such as nitrogen, oxygen or sulfur, and carbocyclic $(C_6-C_{14})$-aryl radicals. Examples of carbocyclic $(C_6-C_{14})$-aryl radicals are phenyl, naphthyl, biphenylyl, anthryl or fluorenyl, where 1-naphthyl, 2-naphthyl and phenyl are preferred. If not stated otherwise, aryl radicals, in particular phenyl radicals, can be unsubstituted or substituted by one or more radicals, preferably one, two or three identical or different radicals. In particular aryl radicals can be substituted by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, such as fluorine, chlorine and bromine, nitro, amino, trifluoromethyl, hydroxyl, methylenedioxy, cyano, hydroxycarbonyl, aminocarbonyl, $(C_1-C_4)$-alkoxycarbonyl, phenyl, phenoxy, benzyl and benzyloxy. Generally, only up to two nitro groups can occur as substituents in the compounds of the formula I according to the invention.

In monosubstituted phenyl radicals, the substituent can be located in the 2-position, the 3-position or the 4-position, the 3- and the 4-position being preferred. If phenyl is disubstituted, the substituents can be in the 2,3-position, 2,4-position, 2,5-position, 2,6-position, 3,4-position or 3,5-position. Preferably, in disubstituted phenyl radicals, the two substituents are arranged in the 3,4-position, relative to the linkage site. In trisubstituted phenyl radicals, the substituents can be in the 2,3,4-position, 2,3,5-position, 2,3,6-position, 2,4,5-position, 2,4,6-position or 3,4,5-position. Similarly, naphthyl radicals and other aryl radicals can be substituted in any desired position, for example a 1-naphthyl radical in the 2-, 3-, 4-, 5-, 6-, 7- and 8-position, a 2-naphthyl radical in the 1-, 3-, 4-, 5-, 6-, 7- and 8-position.

Beside carbocyclic systems, $(C_5-C_{14})$-aryl groups can also be monocyclic or polycyclic, for example bicyclic or tricyclic, aromatic ring systems in which 1, 2, 3, 4 or 5 ring carbon atoms are replaced by heteroatoms, in particular by identical or different heteroatoms from the group consisting of nitrogen, oxygen and sulfur. Examples of heterocyclic $(C_5-C_{14})$-aryl groups and $(C_5-C_{14})$-heteroaryl groups are pyridyl like 2-pyridyl, 3-pyridyl and 4-pyridyl, pyrrolyl like 2-pyrrolyl and 3-pyrrolyl, furyl like 2-furyl and 3-furyl, thienyl like 2-thienyl and 3-thienyl, imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or benzo-fused, cyclopenta-fused, cyclohexa-fused or cyclohepta-fused derivatives of these radicals. The heterocyclic systems can be substituted in all suitable positions by the same substituents as the abovementioned carbocyclic aryl systems.

In the series of these heteroaryl groups, monocyclic or bicyclic aromatic ring systems having 1, 2 or 3 heteroatoms, in particular 1 or 2 heteroatoms, from the group consisting of N, O and S, which can be unsubstituted or substituted by 1, 2 or 3 substituents from the group consisting of $(C_1-C_6)$-alkyl, $(C_1-C_6)$-alkoxy, fluorine, chlorine, nitro, amino, trifluoromethyl, hydroxyl, $(C_1-C_4)$-alkoxycarbonyl, phenyl, phenoxy, benzyloxy and benzyl, are preferred. Particularly preferred are monocyclic or bicyclic aromatic 5-membered to 10-membered ring systems having 1 to 3 heteroatoms, in particular having 1 or 2 heteroatoms, from the group consisting of N, O and S, which can be substituted by 1 to 2 substituents from the group consisting of $(C_1-C_4)$-alkyl, $(C_1-C_4)$-alkoxy, phenyl, phenoxy, benzyl and benzyloxy. More particularly preferred are 5-membered or 6-membered monocyclic heteroaryl groups and 9-membered or 10-membered bicyclic heteroaryl groups containing 1 or 2, in particular 1, heteroatom from the group consisting of N, O and S which are unsubstituted or substituted as described before.

If the two radicals $R^1$— and $R^2$— together represent a bivalent saturated or unsaturated $(C_2-C_9)$-alkylene radical, these two radicals together with the two nitrogen atoms to which they are bonded and the central carbon atom of the guanidino group to which these two nitrogen atoms are bonded, form a monocyclic 1,3-diazaheterocycle which is bonded to the nitrogen atom in the group $(CH_2)_2$—CO—NH via its 2-position. Examples of radicals of such 1,3-diazaheterocycles which can be substituted as indicated in the $(C_2-C_9)$-alkylene radical and also on the guanidino nitrogen atom, are the 2-imidazolyl radical, the 4,5-dihydro-2-imidazolyl radical, the 1,4,5,6-tetrahydro-2-pyrimidinyl radical or the 4,5,6,7-tetrahydro-1H-1,3-diazepin-2-yl radical. If a 5-membered to 7-membered ring is fused to a carbon-carbon bond in the $(C_2-C_9)$-alkylene radical, then the two radicals $R^1$ and $R^2$, together with the two nitrogen atoms to which they are bonded and the central carbon atom of the guanidino group to which these two nitrogen atoms are bonded form a bicyclic heterocycle which is bonded to the nitrogen atom in the group $(CH_2)_2$—CO—NH and which can be substituted as indicated. The fused (or condensed) 5-membered to 7-membered ring can be saturated, mono-unsaturated or di-unsaturated or aromatic. Thus, for example, a cyclopentane ring, cyclohexane ring, cyclohexene ring, cyclohexadiene ring, cycloheptane ring or benzene ring can be condensed. Examples of radicals of such bicyclic heterocycles which can be bonded to the nitrogen atom in the group $(CH_2)_2$—CO—NH are the 1,3a, 4,5,6,6a-hexahydro-1,3-diazapentalen-2-yl radical, the 1H-benzimidazol-2-yl radical, the 3a,4,5,6,7,7a-hexahydro-1H-benzimidazol-2-yl radical, the 4,5,6,7-tetrahydro-1H-benzimidazol-2-yl radical, the 4,7-dihydro-1H-benzimidazol-2-yl radical or the 1H-imidazo[4,5-b]pyridin-2-yl radical. If a condensed ring is substituted and/or if the ($C_2$–$C_9$)-alkylene radical is substituted, they are preferably independently of one another monosubstituted or disubstituted by identical or different radicals $R^3$. If alkyl groups representing $R^1$ and/or $R^2$ are substituted, they are preferably independently of one another monosubstituted or disubstituted, in particular monosubstituted, by identical or different radicals $R^3$.

Optically active carbon atoms present in the compounds of the formula I can independently of one another have the R configuration or the S configuration. The compounds of the formula I can be present in the form of pure enantiomers or pure diastereomers or in the form of enantiomer mixtures, for example in the form of racemates, or of diastereomer mixtures. The present invention relates to both pure enantiomers and enantiomer mixtures as well as to pure diastereomers and diastereomer mixtures. The invention comprises mixtures of two or of more than two stereoisomers of the formula I and all ratios of the stereoisomers in the mixtures. The compounds of the formula I can optionally be present as E isomers or Z isomers. The invention relates to both pure E isomers and pure Z isomers and E/Z mixtures in all ratios. The invention also comprises all tautomeric forms of the compounds of the formula I, for example, beside the form shown in the formula I, also the form in which the acylguanidine unit is present as a —CO—N=C(NHR$^1$)—NR$^2$R$^6$ group, and all other forms which differ by different positions of mobile hydrogen atoms. Diastereomers, including E/Z isomers, can be separated into the individual isomers, for example, by chromatography. Racemates can be separated into the two enantiomers by customary methods, for example, by chromatography on chiral phases or by resolution. Stereochemically unifom compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example carboxyl, are, for example, alkali metal salts or alkaline earth metal salts such as, for example, sodium salts, potassium salts, magnesium salts and calcium salts, and also salts with physiologically tolerable quaternary ammonium ions and acid addition salts with ammonia and physiologically tolerable organic amines, such as, for example, triethylamine, ethanolamine or tris-(2-hydroxyethyl)amine. Compounds of the formula I containing basic groups form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds of the formula I which contain a basic group and an acidic group, for example the guanidino group and a carboxyl group, can be present as zwitterions (betaines), which are likewise included by the present invention.

The physiologically tolerable anion Q$^-$ which is contained in the compounds of the formula I when $R^4$ is an alkyl radical which is substituted by a positively charged ammonium group, is, in particular, a monovalent anion or an eqivalent of a polyvalent anion of a nontoxic, physiologically utilizable, in particular also pharmaceutically utilizable, inorganic or organic acid, for example the anion or an anion equivalent of one of the abovementioned acids suitable for the formation of acid addition salts. Q$^-$ can thus be, for example, one of the anions (or an anion equivalent) from the group consisting of chloride, sulfate, phosphate, acetate, citrate, benzoate, maleate, fumarate, tartrate, methanesulfonate and p-toluenesulfonate.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals, but are suitable, for example, as intermediates for carrying out other chemical modifications of the compounds of the formula I or as starting materials for the preparation of physiologically tolerable salts.

The present invention moreover includes all solvates of compounds of the formula I, for example hydrates or adducts with alcohols, and also derivatives of the compounds of the formula I, for example esters, prodrugs and other physiologically tolerable derivatives, as well as active metabolites of the compounds of the formula I. The invention relates in particular to prodrugs of the compounds of the formula I, which can be converted into compounds of the formula I under physiological conditions. Suitable prodrugs for the compounds of the formula I, i.e. chemically modified derivatives of the compounds of the formula I having properties which are improved in a desired manner, are known to those skilled in the art. More detailed information relating to prodrugs is found, for example, in Fleisher et al, *Advanced Drug Delivery Reviews* 19: 115–130 (1996); H. Bundgaard, Ed., *Design of Prodrugs*, Ed., Elsevier (1985); H. Bundgaard, *Drugs of the Future* 16: 443 (1991); Saulnier et al., *Bioorg. Med. Chem. Lett.* 4: 1985 (1994); Safadi et al, *Pharmaceutical Res.* 10: 1350 (1993). Suitable prodrugs for the compounds of the formula I are especially ester prodrugs of carboxylic acid groups, in particular of the COOH group which is present when $R^4$ in the group COOR$^4$ is hydrogen, for example alkyl esters of this group like ($C_1$–$C_6$)-alkyl esters or ($C_1$–$C_4$)-alkyl esters, and also acyl prodrugs and carbamate prodrugs of acylatable nitrogen-containing groups such as amino groups and in particular the guanidino group. In the acyl prodrugs or carbamate prodrugs, one or more times, for example twice, a hydrogen atom located on a nitrogen atom in these groups is replaced by an acyl group or carbamate group. Suitable acyl groups and carbamate groups for the acyl prodrugs and carbamate prodrugs are, for example, the groups R$^{10}$—CO and R$^{11}$O—CO, in which R$^{10}$ is hydrogen, ($C_1$–$C_{18}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl, in which 1 to 5 carbon atoms can be replaced by heteroatoms such as N, O or S, or ($C_5$–$C_{14}$)-aryl-($C_1$–$C_8$)-alkyl-, in which 1 to 5 carbon atoms in the aryl moiety can be replaced by heteroatoms such as N, O or S, and in which R$^{11}$ has the meanings indicated for R$^{10}$ with the exception of hydrogen.

In the compounds of the formula I, the radicals $R^1$ and $R^2$ are preferably hydrogen or together are a saturated or unsaturated, in particular a saturated, bivalent ($C_2$–$C_5$)-alkylene radical, in particular a ($C_2$–$C_4$)-alkylene radical, especially a ($C_2$–$C_3$)-alkylene radical, which is unsubstituted or is substituted by one or two identical or different radicals from the group consisting of halogen, ($C_1$–$C_6$)-alkyl, ($C_1$–$C_6$)-alkoxy, ($C_6$–$C_{14}$)-aryl, ($C_6$–$C_{14}$)-aryl-($C_1$–$C_6$)-alkyl-, ($C_5$–$C_{14}$)-heteroaryl, ($C_5$–$C_{14}$)-heteroaryl-($C_1$–$C_6$)-alkyl-, ($C_3$–$C_{12}$)-cycloalkyl, ($C_3$–$C_{12}$)-cycloalkyl-($C_1$–$C_6$)-alkyl- and oxo, where a 5-membered to 7-membered saturated or unsaturated ring which is unsubstituted or is substituted by $R^3$, in particular by one or two radicals $R^3$, and which is a carbocyclic ring or heterocyclic ring containing one or two ring nitrogen atoms can be fused to a carbon-carbon bond in the alkylene radical. In the compounds of the formula I, the radicals $R^1$ and $R^2$ are particularly preferably hydrogen or the group $—(CH_2)_p—$, in which p is the numbers 2, 3, 4 or 5, preferably the numbers 2, 3 or 4, particularly preferably the numbers 2 or 3, and which is unsubstituted or is substituted by one or two identical or different radicals from the group consisting of halogen, $(C_1–C_6)$-alkyl, $(C_1–C_6)$-alkoxy, $(C_6–C_{14})$-aryl, $(C_6–C_{14})$-aryl-$(C_1C_6)$-alkyl-, $(C_5–C_{14})$-heteroaryl, $(C_5–C_{14})$-heteroaryl-$(C_1–C_6)$-alkyl-, $(C_3–C_{12})$-cycloalkyl, $(C_3–C_{12})$-cycloalkyl-$(C_1–C_6)$-alkyl- and oxo, where a 5-membered to 7-membered saturated or unsaturated ring which is unsubstituted or is substituted by $R^3$, in particular by one or two radicals $R^3$, and which is a carbocyclic ring or heterocyclic ring containing one or two ring nitrogen atoms, can be fused to a carbon-carbon bond in the group $—(CH_2)_p—$. More particularly preferably the radicals $R^1$ and $R^2$ together are the group $—(CH_2)_p—$, in which p is the numbers 2, 3, 4 or 5, preferably the numbers 2, 3 or 4, particularly preferably the numbers 2 or 3, which preferably is unsubstituted. Especially preferably the radicals $R^1$— and $R^2$— together are the bivalent radical $—CH_2—CH_2—CH_2—$, i. e. $R^1$ and $R^2$ together with the nitrogen atoms to which they are bonded and with the central carbon atom of the guanidino group to which these nitrogen atoms are bonded, form a 1,4,5,6-tetrahydro-2-pyrimidinyl radical.

$R^3$ preferably is $(C_1–C_{10})$-alkyl, $(C_3–C_{20})$-monocycloalkyl, $(C_5–C_{20})$-bicycloalkyl, $(C_5–C_{20})$-tricycloalkyl, $(C_1–C_8)$-alkoxy, $(C_6–C_{14})$-aryl, $(C_5–C_{14})$-heteroaryl, $(C_6–C_{14})$-aryl-$(C_1–C_4)$-alkyl-, $(C_5–C_{14})$-heteroaryl-$(C_1–C_4)$-alkyl-, halogen, trifluoromethyl, cyano, oxo, $—N((C_1–C_4)$-alkyl$)_2$ or $—NH—CO—(C_1–C_4)$-alkyl. More preferably, $R^3$ is $(C_1–C_4)$-alkyl, $(C_3–C_{10})$-monocycloalkyl, $(C_5–C_{12})$-bicycloalkyl, $(C_5–C_{12})$-tricycloalkyl, $(C_1–C_4)$-alkoxy, $(C_6–C_{14})$-aryl, $(C_6–C_{14})$-aryl-$(C_1–C_4)$-alkyl-, halogen, trifluoromethyl, cyano, oxo, $—N((C_1–C_4)$-alkyl$)_2$ or $—NH—CO—(C_1–C_4)$-alkyl. Particularly preferably $R^3$ is $(C_1–C_4)$-alkyl, $(C_3–C_{10})$-monocycloalkyl, $(C_5–C_{12})$-bicycloalkyl, $(C_5–C_{12})$-tricycloalkyl, $(C_1–C_4)$-alkoxy, $(C_6–C_{14})$-aryl, halogen, trifluoromethyl, cyano, oxo, $—N((C_1–C_4)$-alkyl$)_2$ or $—NH—CO—(C_1–C_4)$-alkyl.

$R^4$ is preferably hydrogen or unsubstituted or substituted $(C_1–C_6)$-alkyl, particularly preferably hydrogen or $(C_1–C_6)$-alkyl, which is unsubstituted or substituted by a radical from the group consisting of $(C_1–C_4)$-alkoxy, $(C_1–C_4)$-alkyl-$S(O)_2$— and $—NR^7R^{7'}$, where $R^7$ and $R^{7'}$ independently of one another are hydrogen or $(C_1–C_4)$-alkyl. $R^4$ is particularly preferably hydrogen or unsubstituted or substituted $(C_1–C_4)$-alkyl, moreover preferably hydrogen or $(C_1–C_4)$-alkyl which is unsubstituted or substituted as indicated before.

$R^5$ preferably is $(C_1–C_{20})$-alkyl, $(C_3–C_{20})$-monocycloalkyl, $(C_5–C_{20})$-bicycloalkyl, $(C_5–C_{20})$-tricycloalkyl, $(C_6–C_{14})$-aryl, $(C_5–C_{14})$-heteroaryl, $(C_6–C_{14})$-aryl-$(C_1–C_6)$-alkyl- or $(C_5–C_{14})$-heteroaryl-$(C_1–C_6)$-alkyl-, where the aryl radical, the heteroaryl radical, the alkyl radical, the monocycloalkyl radical, the bicycloalkyl radical and the tricycloalkyl radical each is unsubstituted or is substituted by one, two or three identical or different radicals $R^3$. More preferably $R^5$ is $(C_1–C_{10})$-alkyl, $(C_3–C_{15})$-monocycloalkyl, $(C_5–C_{15})$-bicycloalkyl, $(C_5–C_{15})$-tricycloalkyl, $(C_6–C_{14})$-aryl, $(C_5–C_{14})$-heteroaryl, $(C_6–C_{14})$-aryl-$(C_1–C_6)$-alkyl- or $(C_5–C_{14})$-heteroaryl-$(C_1–C_6)$-alkyl-, where the aryl radical, the heteroaryl radical, the alkyl radical, the monocycloalkyl radical, the bicycloalkyl radical and the tricycloalkyl radical each is unsubstituted or is substituted by one, two or three identical or different radicals $R^3$. Besides these preferences, a preferred group of radicals $R^5$ is formed by the radicals $(C_3–C_{20})$-monocycloalkyl, $(C_5–C_{20})$-bicycloalkyl and $(C_5–C_{20})$-tricycloalkyl which can be substituted or otherwise modified as indicated above and which moreover preferred are $(C_5–C_{15})$-monocycloalkyl, $(C_5–C_{15})$-bicycloalkyl, $(C_5–C_{15})$-tricycloalkyl. Another preferred group of radicals $R^5$ is formed by the radicals $(C_1–C_{20})$-alkyl, $(C_6–C_{14})$-aryl, $(C_5–C_{14})$-heteroaryl, $(C_6–C_{14})$-aryl-$(C_1–C_6)$-alkyl- or $(C_5–C_{14})$-heteroaryl-$(C_1–C_6)$-alkyl-, of which $(C_6–C_{14})$-aryl and $(C_5–C_{14})$-heteroaryl are preferred, which can be substituted or otherwise modified as indicated above. A particularly preferred groups of radicals $R^5$ is formed by the radicals phenyl and naphthyl, i.e. phenyl, 1-naphthyl and 2-naphthyl, which can be unsubstituted or substituted as indicated above.

$R^6$ is preferably hydrogen or $(C_1–C_6)$-alkyl-O—CO—, particularly preferably hydrogen or $(C_1–C_4)$-alkyl-O—CO—, in particular hydrogen.

Preferred compounds of the formula I are those compounds in which one or more of the radicals have preferred meanings or have one specific or some specific of their respective denotations, all combinations of such preferred meanings or specific denotations being a subject of the present invention.

Particularly preferred compounds of the formula I are those compounds in which:

$R^1$ and $R^2$ are hydrogen or together are a saturated or unsaturated bivalent $(C_2–C_5)$-alkylene radical, in particular hydrogen or together the group $—(CH_2)_p—$, in which p is the numbers 2, 3, 4 or 5, where the $(C_2–C_5)$-alkylene radical and the group $—(CH_2)_p—$ are unsubstituted or are substituted by a radical from the group consisting of halogen, $(C_1–C_6)$-alkyl, $(C_1–C_6)$-alkoxy, $(C_6–C_{14})$-aryl, $(C_6–C_{14})$-aryl-$(C_1–C_6)$-alkyl-, $(C_5–C_{14})$-heteroaryl, $(C_5–C_{14})$-heteroaryl-$(C_1–C_6)$-alkyl-, $(C_3–C_{12})$-cycloalkyl, $(C_3–C_{12})$-cycloalkyl-$(C_1–C_6)$-alkyl- and oxo, and where a 5-membered to 7-membered saturated or unsaturated ring which is unsubstituted or substituted by $R^3$, in particular by one or two radicals $R^3$, and which is a carbocyclic ring or heterocyclic ring containing one or two ring nitrogen atoms, can be fused to a carbon-carbon bond in the $(C_2–C_5)$-alkylene radical and in the group $—(CH_2)_p—$;

$R^3$ is $(C_1–C_{10})$-alkyl, $(C_3–C_{20})$-monocycloalkyl, $(C_5–C_{20})$-bicycloalkyl, $(C_5–C_{20})$-tricycloalkyl, $(C_1–C_8)$-alkoxy, $(C_6–C_{14})$-aryl, $(C_5–C_{14})$-heteroaryl, $(C_6–C_{14})$-aryl-$(C_1–C_4)$-alkyl-, $(C_5–C_{14})$-heteroaryl-$(C_1–C_4)$-alkyl-, halogen, trifluoromethyl, cyano, oxo, $—N((C_1–C_4)$-alkyl$)_2$ or $—NH—CO—(C_1–C_4)$-alkyl;

$R^4$ is hydrogen or $(C_1–C_6)$-alkyl which is unsubstituted or is substituted by a radical from the group consisting of $(C_1–C_4)$-alkoxy, $(C_1–C_4)$-alkyl-$S(O)_2$— and $NR^7R^{7'}$, where $R^7$ and $R^{7'}$ independently of one another are hydrogen or $(C_1–C_4)$-alkyl;

$R^5$ is $(C_1–C_{20})$-alkyl, $(C_3–C_{20})$-monocycloalkyl, $(C_5–C_{20})$-bicycloalkyl, $(C_5–C_{20})$-tricycloalkyl, $(C_6–C_{14})$-aryl, $(C_5–C_{14})$-heteroaryl, $(C_6–C_{14})$-aryl-$(C_1–C_6)$-alkyl- or $(C_5–C_{14})$-heteroaryl-$(C_6)$-alkyl-, where the aryl radical, the heteroaryl radical, the alkyl radical, the monocycloalkyl radical, the bicycloalkyl radical and the tricycloalkyl radical each is unsubstituted or is substituted by one, two or three radicals $R^3$.

$R^6$ is hydrogen or $(C_1–C_6)$-alkyl-O—CO—; in all their stereoisomeric forms and mixtures thereof in all ratios, and their physiologically tolerable salts and their prodrugs.

Very particularly preferred compounds of the formula I are those compounds in which:

$R^1$ and $R^2$ are hydrogen or together are a saturated or unsaturated bivalent $(C_2-C_4)$-alkylene radical, in particular hydrogen or together the group —$(CH_2)_p$—, in which p is the numbers 2, 3 or 4, where the $(C_2-C_4)$-alkylene radical and the group —$(CH_2)_p$— are unsubstituted or are substituted by a radical from the group consisting of halogen, $(C_1-C_6)$-alkyl, $(C_1-C_6)$-alkoxy, $(C_6-C_{14})$-aryl, $(C_6-C_{14})$-aryl-$(C_1C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$-alkyl- and oxo, and where a 5-membered to 7-membered saturated or unsaturated ring which is unsubstituted or is substituted by $R^3$, in particular by one or two radicals $R^3$, and which is a carbocyclic ring or heterocyclic ring containing one or two ring nitrogen atoms, can be fused to a carbon-carbon bond in the $(C_2-C_4)$-alkylene radical and in the group —$(CH_2)_p$—;

$R^3$ is $(C_1-C_4)$-alkyl, $(C_3-C_{10})$-monocycloalkyl, $(C_5-C_{12})$-bicycloalkyl, $(C_5-C_{12})$-tricycloalkyl, $(C_1-C_4)$-alkoxy, $(C_6-C_{14})$-aryl, $(C_6-C_{14})$-aryl-$(C_1-C_4)$-alkyl-, halogen, trifluoromethyl, cyano, oxo, —$N((C_1-C_4)$-alkyl$)_2$ or —NH—CO—$(C_1-C_4)$-alkyl;

$R^4$ is hydrogen or $(C_1-C_6)$-alkyl;

$R^5$ is $(C_1-C_{10})$-alkyl, $(C_3-C_{15})$-monocycloalkyl, $(C_5-C_{15})$-bicycloalkyl, $(C_5-C_{15})$-tricycloalkyl, $(C_6-C_{14})$-aryl, $(C_5-C_{14})$-heteroaryl, $(C_6-C_{14})$-aryl-$(C_1-C_6)$-alkyl- or $(C_5-C_{14})$-heteroaryl-$(C_1-C_6)$-alkyl-, where the aryl radical, the heteroaryl radical, the alkyl radical, the monocycloalkyl radical, the bicycloalkyl radical and the tricycloalkyl radical each is unsubstituted or is substituted by one, two or three radicals $R^3$;

$R^6$ is hydrogen or $(C_1-C_4)$-alkyl-O—CO—; in all their stereoisomeric forms and mixtures thereof in all ratios, and their physiologically tolerable salts and their prodrugs.

Especially preferred compounds of the formula I are those in which:

$R^1$ and $R^2$ are hydrogen or together are a saturated or unsaturated bivalent $(C_2-C_3)$-alkylene radical, in particular hydrogen or together the group —$(CH_2)_p$—, in which p is the numbers 2 or 3, where the $(C_2-C_3)$-alkylene radical and the group —$(CH_2)_p$— are unsubstituted or are substituted by a radical from the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$-alkyl- and oxo, and where a 5-membered to 7-membered saturated or unsaturated ring which is unsubstituted or is substituted by $R^3$, in particular by one or two radicals $R^3$, and which is a carbocyclic ring or heterocyclic ring containing one or two ring nitrogen atoms, can be fused to a carbon-carbon bond in the $(C_2-C_3)$-alkylene radical and in the group —$(CH_2)_p$—;

$R^3$ is $(C_1-C_4)$-alkyl, $(C_3-C_{10})$-monocycloalkyl, $(C_5-C_{12})$-bicycloalkyl, $(C_5-C_{12})$-tricycloalkyl, $(C_1-C_4)$-alkoxy, $(C_6-C_{14})$-aryl, halogen, trifluoromethyl, cyano, oxo, —$N((C_1-C_4)$-alkyl$)_2$ or —NH—CO—$(C_1-C_4)$-alkyl;

$R^4$ is hydrogen or $(C_1-C_6)$-alkyl;

$R^5$ is $(C_1-C_{10})$-alkyl, $(C_3-C_{15})$-monocycloalkyl, $(C_5-C_{15})$-bicycloalkyl, $(C_5-C_{15})$-tricycloalkyl, $(C_6-C_{14})$-aryl, $(C_5-C_{14})$-heteroaryl, $(C_6-C_{14})$-aryl-$(C_1-C_6)$-alkyl- or $(C_5-C_{14})$-heteroaryl-$(C_1-C_6)$-alkyl-, where the aryl radical, the heteroaryl radical, the alkyl radical, the monocycloalkyl radical, the bicycloalkyl radical and the tricycloalkyl radical each is unsubstituted or is substituted by one, two or three radicals $R^3$;

$R^6$ is hydrogen or $(C_1-C_4)$-alkyl-O—CO—; in all their stereoisomeric forms and mixtures thereof in all ratios, and their physiologically tolerable salts and their prodrugs.

Moreover preferred compounds of the formula I are those in which $R^5$ is $(C_6-C_{14})$-aryl or $(C_5-C_{14})$-heteroaryl, preferably $(C_6-C_{14})$-aryl, where the aryl radical and the heteroaryl radical each is unsubstituted or is substituted by one, two or three identical or different radicals $R^3$ and preferably is unsubstituted or substituted by one or two identical or different radicals $R^3$, in all their stereoisomeric forms and mixtures thereof in all ratios, and their physiologically tolerable salts and their prodrugs. Even more preferred compounds of the formula I are those in which $R^5$ is a naphthyl radical, such as a 1-naphthyl radical or a 2-naphthyl radical, which is unsubstituted or is substituted by one, two or three radicals $R^3$, and which preferably is unsubstituted, such as an unsubstituted 1-naphthyl radical or an unsubstituted 2-naphthyl radical, in all their stereoisomeric forms and mixtures thereof in all ratios, and their physiologically tolerable salts and their prodrugs.

Preferred compounds of the formula I are additionally those in which the carbon atom to which the two groups $R^4$O—CO— and $R^5$—SO_2—NH— are bonded has the S configuration, in all their stereoisomeric forms and mixtures thereof in all ratios, and their physiologically tolerable salts and their prodrugs.

A specific group of compounds of the formula I is formed by compounds in which:

$R^1$ and $R^2$ independently of one another are hydrogen or $(C_1-C_6)$-alkyl which is unsubstituted or substituted by $R^3$, or in which the radicals $R^1$— and $R^2$— together are a saturated or unsaturated bivalent $(C_2-C_9)$-alkylene radical, for example the group —$(CH_2)_p$—, in which p is 2, 3, 4, 5, 6, 7, 8 or 9, which is unsubstituted or is substituted by one or more groups from the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, where a 5-membered to 7-membered saturated or unsaturated ring which is unsubstituted or is substituted by $R^3$, in particular by one or two radicals $R^3$, and which is a carbocyclic ring or a heterocyclic ring containing one or two ring nitrogen atoms, can be fused to a carbon-carbon bond in the $(C_2-C_9)$-alkylene radical;

$R^3$ is $(C_1-C_8)$-alkyl, $(C_1-C_8)$-alkoxy, $(C_5-C_{14})$-aryl, $(C_5-C_{14})$-aryl-$(C_1-C_4)$-alkyl, $(C_5-C_{14})$-heteroaryl, $(C_5-C_{14})$-heteroaryl-$(C_1-C_4)$-alkyl, halogen, trifluoromethyl, hydroxyl, oxo, nitro, amino, NH—$(C_1-C_4)$-alkyl, N-$((C_1-C_4)$-alkyl$)_2$, NH—CO—$(C_1-C_4)$-alkyl, CO—$(C_1-C_4)$-alkyl;

$R^4$ is hydrogen, $(C_1-C_6)$-alkyl-CO—O—$(C_1-C_4)$-alkyl or $(C_1-C_6)$-alkyl, which is unsubstituted or is substituted by a radical from the group consisting of hydroxyl, $(C_1-C_4)$-alkoxy, $(C_1-C_4)$-alkyl-S(O)$_2$, $NR^7R^{7'}$ and $N^+R^7R^{7'}R^{7''}Q^-$, where $R^7$, $R^{7'}$ and $R^{7''}$ independently of one another are hydrogen, $(C_1-C_6)$-alkyl, $(C_5-C_{14})$-aryl or $(C_5-C_{14})$-aryl-$(C_1-C_6)$-alkyl and $Q^-$ is a physiologically tolerable anion, or in which $R^4$ is one of the radicals:

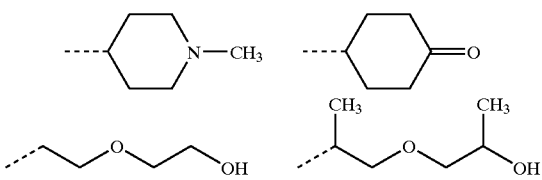

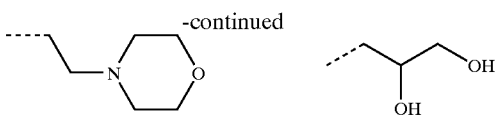

in which the free bonds, via which the radicals are bonded, are indicated by dashed lines;

$R^5$ is $(C_1-C_{20})$-alkyl, $(C_5-C_{20})$-monocycloalkyl, $(C_5-C_{20})$-bicycloalkyl, $(C_5-C_{20})$-tricycloalkyl, $(C_6-C_{14})$-aryl, $(C_5-C_{14})$-heteroaryl, $(C_6-C_{14})$-aryl-$(C_1-C_6)$-alkyl or $(C_5-C_{14})$-heteroaryl-$(C_1-C_6)$-alkyl, wherein one or more carbon atoms, in particular one, two, three, or four carbon atoms, of the alkyl radical, the monocycloalkyl radical, the bicycloalkyl radical and the tricycloalkyl radical may be replaced by identical or different atoms selected from the group consisting of nitrogen, oxygen and sulfur, and wherein the aryl radical, the heteroaryl radical, the alkyl radical, the monocycloalkyl radical, the bicycloalkyl radical and the tricycloalkyl radical each is unsubstituted or is substituted by one, two or three radicals R;

$R^6$ is hydrogen, $(C_1-C_6)$-alkyl-O—CO, hydroxyl, $(C_1-C_6)$-alkyl-O—CO—O or nitro;

in all their stereoisomeric forms and mixtures thereof in all ratios, and their physiologically tolerable salts and their prodrugs.

The present invention also relates to processes for the preparation of the compounds of the formula I. The compounds can generally be prepared, for example in the course of a convergent synthesis, by linkage of two or more fragments which can be derived retrosynthetically from the formula I. In the preparation of the compounds of the formula I it can generally be advantageous or necessary in the course of the synthesis to introduce functional groups which could lead to undesired reactions or side reactions in the respective synthesis step, in the form of precursors which are later converted into the desired functional groups, or to temporarily block functional groups by a protective group strategy suited to the synthesis problem. Such strategies are well known to one skilled in the art (see, for example, Greene and Wuts, *Protective Groups in Organic Synthesis*, Wiley, (1991)). As examples of precursor groups nitro groups and cyano groups may be mentioned which can later be converted by reduction, for example by catalytic hydrogenation, into amino groups and aminomethyl groups, respectively.

The compounds of the formula I can be prepared, for example, by linking in a manner known per se a carboxylic acid or carboxylic acid derivative of the formula II

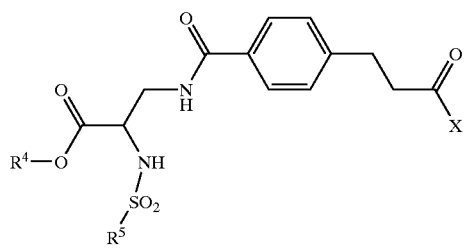

in which $R^4$ and $R^5$ are defined as indicated for the formula I, or in which alternatively functional groups are present in the form of precursors which are later converted into the groups present in the compounds of the formula I, or in which functional groups are present in protected form, and in which X is a nucleophilically substitutable leaving group, with a guanidine or guanidine derivative of the formula III

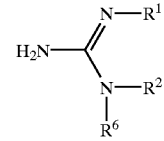

in which $R^1$, $R^2$ and $R^6$ are defined as indicated for the formula I, or alternatively functional groups are present in the form of precursors which are later converted into the groups present in the compounds of the formula I, or functional groups are present in protected form.

The group COX in the formula II is preferably the carboxylic acid group COOH or an activated carboxylic acid derivative. X, for example, is hydroxyl or halogen, in particular chlorine or bromine, alkoxy, preferably methoxy or ethoxy, aryloxy, for example phenoxy or pentafluorophenoxy, phenylthio, methylthio, 2-pyridylthio or a radical of a nitrogen heterocycle bonded via a nitrogen atom, in particular of an azole, such as, for example, 1-imidazolyl. X can furthermore be, for example, $((C_1-C_4)$-alkyl)-O—CO—O— or tolylsulfonyloxy and the activated acid derivative can thus be a mixed anhydride.

If X is hydroxyl, i. e. if the guanidine of the formula III is reacted with a carboxylic acid, then the carboxylic acid is expediently first activated. The activation can be carried out, for example, with dicyclohexylcarbodiimide (DCCl) or with O-((cyano(ethoxycarbonyl)-methylen)amino)-1,1,3,3-tetramethyluronium tetrafluoroborate (TOTU; König et al, Proc. 21st Europ. Peptide Symp., Eds. Giralt, Andreu (1990), Escom, Leiden, p. 143 (1991)) or other activating reagents customary in peptide chemistry.

Beside the free guanidines of the formula ill, guanidinium salts can also be employed in the reaction with the compounds of the formula II, from which the free guanidines are then prepared in situ or in a separate step by means of a base. The reaction of an activated carboxylic acid derivative of the formula II with the guanidine (derivative) of the formula III is preferably carried out in a manner known per se in a protic or aprotic polar, but inert, organic solvent. In this case solvents like methanol, isopropanol, tert-butanol, dimethylformamide or tetrahydrofuran at temperatures from 0° C. up to the boiling temperature of these solvents have proven suitable, for example, in the reaction of methyl esters (X=methoxy) or of ethyl esters (X=ethoxy) with guanidines. The reactions of compounds of the type COX with salt-free guanidines are advantageously carried out in aprotic inert solvents such as dimethylformamide, tetrahydrofuran, dimethoxyethane or dioxane, if appropriate with addition of a base such as, for example, potassium tert-butoxide or sodium methoxide. However, water can also be used as a solvent in the reaction of compounds of the formula II with guanidines, for example when using a base such as sodium hydroxide. If X is, for example, chlorine the reaction is advantageously carried out with addition of an acid scavenger, for example an additional base or in the presence of excess guanidine (derivative), for binding the resulting hydrohalic acid. The reaction mixture is worked up and, if desired, the reaction product is then purified by the customary processes familiar to those skilled in the art.

Protective groups optionally still present in the products obtained from the compounds of the formulae II and III are then removed by standard processes. For example, tert-butyl ester groups are converted into the carboxylic acid groups by treatment with trifluoroacetic acid, benzyl groups are removed by hydrogenation or fluorenylmethoxycarbonyl groups are removed by secondary amines. If desired, further reactions are then carried out by standard processes, for example acylation reactions or esterification reactions. In addition, a conversion into a physiologically tolerable salt or prodrug can then be carried out by known processes.

The starting components of the formulae II and III, which are linked to give the compounds of the formula I, are commercially available or can be prepared by or analogously to processes described in the literature. The preparation of the starting components of the formula II is illustrated by way of example in the following scheme (Scheme 1), the present invention not being restricted to this synthesis or these starting components. It does not cause any problems to those skilled in the art to carry out the modifications of the synthesis shown, which are necessary for the preparation of other compounds according to the invention.

Scheme 1

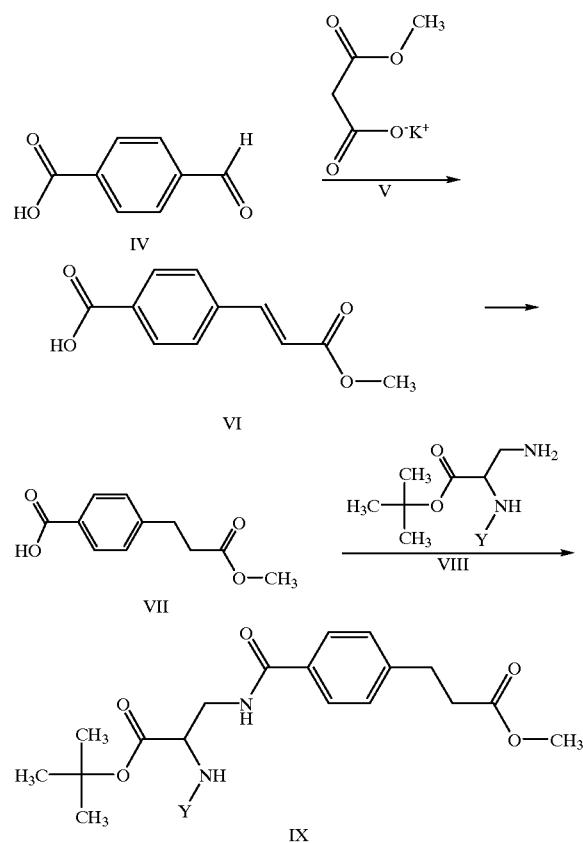

Thus, the carboxybenzaldehyde of the formula IV can be reacted, for example in the presence of pyridine and piperidine, with the malonic acid ester salt of the formula V to give the cinnamic acid derivative of the formula VI which, after hydrogenation, for example in the presence of palladium on carbon, gives the compound of the formula VII. After activation of the carboxylic acid group the compound of the formula VII can be condensed with the 2,3-diaminopropionic acid derivative of the formula VIII to give the compound of the formula IX (Scheme 1). The condensation can be carried out, for example, in the presence of TOTU or another customary agent for activating carboxylic acids.

In the formula VIII, Y can be the group $R^5$—$SO_2$— which is present in the final compounds of the formula I according to the invention and which can then remain in the molecule, or Y can be a group which temporarily protects the amino group in the 2-position and which in a later stage is removed to give a free amino group which can then be converted into an $R^5$—$SO_2$—NH group by standard procedures for the preparation of sulfonamides, for example by reacting the free amine with a sulfonyl chloride of the formula $R^5$—$SO_2$—Cl. An example of a protecting group representing Y is the benzyloxycarbonyl group (Z group) which can be removed by catalytic hydrogenation. Sulfonyl chlorides of the formula $R^5$—$SO_2$-Cl and other sulfonic acid derivatives suitable for introducing the group $R^5$—$SO_2$ are commercially available or can be prepared according to or analogously to procedures described in the literature. Instead of the tert-butyl ester present in the compounds of formula VIII and IX other esters can be present which either only temporarily protect the acid group or which can also be present in the final compounds of the formula I according to the invention and can remain in the molecule. Compounds analogous to the compound of the formula VI can also be obtained by other processes for the conversion of a carbonyl group into an alkene, for example by a Wittig reaction.

The compounds of the formula IX are examples of compounds of the formula II in which X is methoxy. These compounds and analogous compounds which are obtained from the synthesis described above and which contain a group that is an activated carboxylic acid derivative, can be reacted directly with the compounds of the formula III. The compounds obtained in the above synthesis, however, can also first be converted under standard conditions by cleavage of the methyl ester group or another ester group present in the position concerned in the compounds of the formula IX, into the corresponding carboxylic acids which are then reacted with the guanidines of the formula III after in situ activation, for example with TOTU or DCCl, or after conversion into an activated carboxylic acid derivative. If, as activated acid derivatives, it is intended to prepare, for example, the carboxylic acid chlorides (formula II, X=Cl), this conversion can be carried out, for example, by using thionyl chloride. If it is intended to prepare, for example, the methyl esters (formula II, X=methoxy) from the carboxylic acids, this can be carried out by treatment with gaseous hydrogen chloride in methanol. Other activated acid derivatives can be prepared in a manner known per se from the carboxylic acid chlorides or directly from the carboxylic acids on which they are based (formula II, X=OH). Example are the imidazolides (formula II, X=1-imidazolyl) which are obtained by treating the acids with carbonyldiimidazole (cf. Staab, Angew. Chem. Int. Ed. Engl. 1, 351–367 (1962)), or the mixed anhydrides which are obtained, for example, by reaction with chloroformic acid esters such as ethyl chloroformate or with tosyl chloride in the presence of amines such as triethylamine in an inert solvent. A number of suitable methods for the preparation of activated carboxylic acid derivatives are indicated with details of source literature in J. March, Advanced Organic Chemistry, Third Edition, John Wiley & Sons, p. 350 (1985).

The compounds of the formula I are valuable pharmaceutical active ingredients which are suitable, for example, for the therapy and prophylaxis of bone disorders, tumor diseases or cardiovascular disorders. The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations which permit enteral or parenteral administration and which, as active constituent, contain an efficacious dose of at least one compound of the formula I and/or its physiologically tolerable salts and/or its prodrugs in addition to customary pharmaceutically innocuous carriers and/or additives.

The present invention therefore also relates to the compounds of the formula I and/or their physiologically tolerable salts and/or their prodrugs for use as pharmaceuticals, to the use of the compounds of the formula I and/or their physiologically tolerable salts and/or their prodrugs for the production of pharmaceuticals for the therapy and prophylaxis of the diseases mentioned above or below, for example for the therapy and prophylaxis of bone disorders, and also to the use of the compounds of the formula I and/or their physiologically tolerable salts and/or their prodrugs for the therapy and prophylaxis of these diseases. The present invention furthermore relates to pharmaceutical preparations or pharmaceutical compositions which contain an efficacious dose of at least one compound of the formula I and/or its physiologically tolerable salts and/or its prodrugs in addition to a customary pharmaceutically innocuous carrier.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically inert inorganic or organic carriers being used in addition to the compound(s) of the formula I and/or its (their) physiologically tolerable salts and/or its (their) prodrugs. For the production of pills, tablets, coated tablets and hard gelatin capsules, it is possible to use, for example, lactose, corn starch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain approximately 0.5 to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is 0.2 to 500 mg, preferably 1 to 200 mg.

In addition to the active ingredients and carriers, the pharmaceutical preparations can additionally contain additives, such as, for example, fillers, disintegrants, binders, lubricants, wetting agents, stabilizers, emulsifiers, preservatives, sweeteners, colorants, flavorings or aromatizers, thickeners, diluents, buffer substances, and also solvents or solubilizers or agents for achieving a depot effect, and also salts for altering the osmotic pressure, coating agents or antioxidants. They can also contain two or more compounds of the formula I and/or their physiologically tolerable salts and/or their prodrugs. Furthermore, in addition to at least one compound of the formula I and/or its physiologically tolerable salts and/or its prodrugs, they can also contain one or more other therapeutically or prophylactically active ingredients.

The compounds of the formula I are antagonists of the vitronectin receptor and inhibitors of cell adhesion. They have, for example, the ability to inhibit the binding of osteoclasts to the bone surface and thereby inhibit bone resorption by osteoclasts. The action of the compounds of the formula I can be demonstrated, for example, in an assay in which the inhibition of the binding of vitronectin to cells which contain the vitronectin receptor is determined. Details of such an assay are given below. As vitronectin receptor antagonists, the compounds of the formula I and their physiologically tolerable salts and their prodrugs are generally suitable for the therapy and prophylaxis of diseases which are based on the interaction between vitronectin receptors and their ligands in cell-cell interaction processes or cell-matrix interaction processes, or which can be influenced by an inhibition of interactions of this type, or for their prevention, alleviation or cure an inhibition of interactions of this type is desired. As explained at the beginning, such interactions, for example, play a part in bone resorption, in angiogenesis or in the proliferation of cells of the vascular smooth musculature. The compounds of the formula I and their physiologically tolerable salts and their prodrugs are therefore suitable, for example, for the alleviation or cure of diseases which are caused at least partially by an undesired extent of bone resorption, angiogenesis or proliferation of cells of the vascular smooth musculature.

Bone diseases for whose treatment and prevention the compounds of the formula I according to the invention can be employed are especially osteoporosis, hypercalcemia, osteopenia, for example caused by metastases, dental disorders, hyperparathyroidism, periarticular erosions in rheumatoid arthritis and Paget's disease. In addition, the compounds of the formula I can be used for the alleviation, avoidance or therapy of bone disorders which are caused by a glucocorticoid, steroid or corticosteroid therapy or by a lack of sex hormone(s). All these disorders are characterized by bone loss, which is based on the inequilibrium between bone formation and bone destruction and which can be favorably influenced by the inhibition of bone resorption by osteoclasts. The compounds of the formula I and/or their physiologically tolerable salts and/or their prodrugs can also favorably be used as inhibitor of bone resorption, for example in the therapy or prophylaxis of osteoporosis, in combination with conventional osteoporosis treatments, for example in combination with bisphosphonates, estrogens, estrogen/progesterone, estrogen agonists/antagonists, calcitonin, vitamin D analogues, parathyroid hormone, growth hormone secretagogues, or sodium fluoride. Administration of the compounds of the formula I and/or their physiologically tolerable salts and/or their prodrugs and of other active ingredients effective in the treatment or prophylaxis of osteoporosis like those listed before can take place simultaneously or sequentially, in any order, and jointly or separately. For use in such a combination treatment or prophylaxis the compounds of the formula I and/or their physiologically tolerable salts and/or their prodrugs and one or more other active ingredients like those listed before can together be present in a single pharmaceutical preparation, for example tablets or granules, or can be present in two or more separate pharmaceutical preparations which can be contained in a single package or in two or more separate packages. The use of the compounds of the formula I and/or their physiologically tolerable salts and/or their prodrugs in such a combination therapy or prophylaxis and their use in the production of pharmaceuticals for such a combination therapy or prophylaxis are also subjects of the present invention. The invention furthermore relates to pharmaceutical preparations which comprise efficacious amounts of at least one compound of the formula I and/or its physiologically tolerable salts and/or its prodrugs together with at least one other active ingredient effective in the treatment or prophylaxis of osteoporosis or in the inhibition of bone resorption like those listed before, together with a customary pharmaceutically innocuous carrier. The above explanations on pharmaceutical preparations correspondingly apply to such pharmaceutical combination preparations.

Apart from use as inhibitors of bone resorption by osteoclasts, the compounds of the formula I and their physiologically tolerable salts and their prodrugs can be used as inhibitors of tumor growth and tumor metastasis, as antiinflammatories, for the therapy or prophylaxis of cardiovascular disorders such as arteriosclerosis or restenosis, or for the therapy or prophylaxis of nephropathies or retinopathies, such as, for example, diabetic retinopathy. As inhibitors of tumor growth or tumor metastasis the compounds of the formula I and/or their physiologically tolerable salts and/or their prodrugs can also favorably be used in combination with conventional cancer therapy. Examples of conventional cancer therapy are given in Bertino (Editor), Encyclopedia of Cancer, Academic Press (1997). All the above statements relating to the use of the compounds of formula I in combination with conventional osteoporosis therapy like, for example, possible modes of administration and pharmaceutical combination preparations, correspondingly apply to the use of the compounds of formula I in combination with conventional cancer therapy.

When using the compounds of the formula I, the dose can vary within wide limits and, as is customary, is to be suited to the individual conditions in each individual case. It depends, for example, on the compound employed or on the nature and severity of the disease to be treated and on whether an acute or chronic condition is treated or whether prophylaxis is carried out. In the case of oral administration, the daily dose is in general 0.01 to 100 mg/kg, preferably 0.1 to 50 mg/kg, in particular 0.1 to 5 mg/kg, for example 0.3 to 0.5 mg/kg to achieve effective results in an adult weighing about 75 kg (in each case in mg per kg of body weight). Also in the case of intravenous administration the daily dose is in general approximately 0.01 to 100 mg/kg, preferably 0.05 to 10 mg/kg (in each case per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Apart from use as pharmaceutical active ingredients, the compounds of the formula I can also be used as vehicles or carriers of active ingredients in order to transport the active ingredient specifically to the site of action (=drug targeting; see, for example, R. C. Juliano, Targeted Drug Delivery, Handbook of Experimental Pharmacology, Vol. 100, Ed. Born, G. V. R. et al., Springer Verlag). The active ingredients to be transported are in particular those which can be used for the treatment of the abovementioned diseases.

The compounds of the formula I and their salts can furthermore be employed for diagnostic purposes, for example in in vitro diagnoses, and as auxiliaries in biochemical investigations in which blocking of the vitronectin receptor or influencing of cell-cell or cell-matrix interactions is desired. They can furthermore be used as synthesis intermediates for the preparation of other compounds, in particular of other pharmaceutical active ingredients, which are obtainable from the compounds of the formula I, for example by modification or introduction of radicals or functional groups.

The invention is described in more detail in the following illustrative examples. Although the examples may represent only selected embodiments of the invention, it should be understood that the following examples are illustrative and not limiting.

EXAMPLES

The products were identified via mass spectra (MS) and/or NMR spectra. Depending on how the last synthesis step and/or workup procedures, for example freeze-drying, were carried out, in some cases the compounds were obtained partially or completely in the form of a salt, for example in the form of an acetic acid salt, trifluoroacetic acid salt or hydrochloric acid salt.

Example 1

(2S)-2-(Naphthalene-1-sulfonylamino)-3-(4-(2-(1,4, 5,6-tetrahydropyrimidin-2-ylcarbamoyl)-ethyl)-benzoylamino)-propionic acid

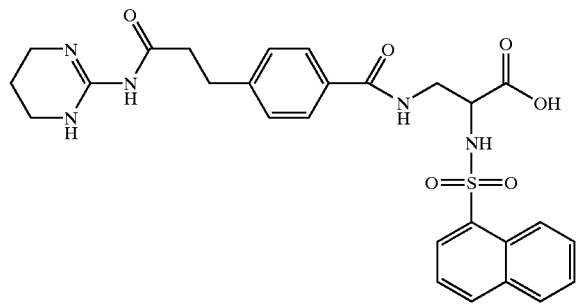

a) 4-(2-Methoxycarbonyl-vinyl)benzoic acid 18.74 g (0.12 mol) of monomethyl malonate potassium salt were suspended in 18 ml of pyridine. 15.01 g (0.1 mol) of 4-carboxybenzaldehyde and 0.85 g (0.01 mol) of piperidine were added at room temperature with stirring. The mixture was refluxed until the evolution of $CO_2$ was complete (about 2 hours), then a further 60 ml of pyridine were added and the mixture was stirred under reflux for a further 1 hour. The reaction mixture was treated with stirring with 500 ml of ice and 110 ml of conc. hydrochloric acid. After addition was complete, the mixture was stirred for a further 20 minutes, and the product was filtered off with suction, washed with water and recrystallized from isopropanol. Yield 12.85 g.

$^1$H-NMR (200 MHz, $d_6$-DMSO): δ=3.75 (s, 3H, $OCH_3$); 6.76 (d, J=15 Hz, 1H, C$\underline{H}$COOCH$_3$); 7.73 (d, J=15 Hz, 1H, Ar—C$\underline{H}$); 7.84 (d, J=9 Hz, 2H, Ar—H); 7.98 (d, J=9 Hz, 2H, Ar—H); 13.11 (s, broad, 1H, COOH). MS (Cl$^+$): m/e=207.2 (M+H$^+$).

HPLC: RP18, Nucleosil 300-5-C18, 250×4 mm; buffer A: $H_2O$, 0.1% trifluoroacetic acid (TFA); buffer B: acetonitrile (80% v/v)/$H_2O$ (20% v/v), 0.1% TFA; gradient: first 5 min 90% buffer A/10% buffer B, then during 20 min to 90% buffer B, then 5 min 90% buffer B; flow rate 1 ml/min; $R_t$=18.05 min.

b) 4-(2-Methoxycarbonyl-ethyl)benzoic acid 8 g (38.8 mmol) of 4-(2-methoxycarbonyl-vinyl)benzoic acid were suspended in 250 ml of dioxane and hydrogenated for 7 hours at room temperature over Pd/C (10% strength) at 1 bar of hydrogen. The mixture was filtered and the solvent was removed in vacuo. Yield 8.05 g.

$^1$H-NMR (200 MHz, d6-DMSO): δ=2.67 (t, J=8 Hz, 2H, C$\underline{H}_2$—COOCH$_3$); 2.93 (t, J=8 Hz, 2H, Ar—C$\underline{H}_2$); 3.59 (s, 3H, OCH$_3$); 7.35 (d, 2H, Ar—H); 7.86 (d, J=9 Hz, 2H, Ar—H); 12.80 (s, broad, 1H, COOH). MS (Cl$^+$): m/e=209.2 (M+H$^+$).

HPLC: RP18, Nucleosil 300-5-C18, 250×4 mm; buffer A: H$_2$O, 0.1% TFA; buffer B: acetonitrile (80% v/v)/H$_2$O (20% v/v), 0.1% TFA; gradient: first 5 min 90% buffer A, 10% buffer B, then during 20 min to 90% buffer B, then 5 min 90% buffer B; flow rate 1 ml/min; R$_t$=17.03 min.

c) tert-Butyl (2S)-2-benzyloxycarbonylamino-3-(4-(2-methoxycarbonyl-ethyl)-benzoylamino)propionate 354 mg (1.7 mmol) of 4-(2-methoxycarbonyl-ethyl)benzoic acid and 500 mg (1.7 mmol) of tert-butyl (2S)-3-amino-2-benzyloxycarbonylaminopropionate were dissolved in 3 ml of dimethylformamide and treated with 557 mg (1.7 mmol) of O-((cyano-(ethoxycarbonyl)-methylidene)amino)-1,1,3,3-tetramethyluronium tetrafluoroborate (TOTU) and 204 mg (1.7 mmol) of diisopropylethylamine, and the mixture was stirred at room temperature for 7 hours at pH 7–8. The solvent was removed in vacuo, the residue was dissolved in ethyl acetate and the solution was washed three times each with KHSO$_4$ solution and NaHCO$_3$ solution until neutral. The organic phase was separated off and dried and the solvent was removed by distillation in vacuo. Yield 770 mg. MS (ES$^+$): m/e=485.2 (M+H$^+$).

d) (2S)-2-Amino-3-(4-(2-methoxycarbonyl-ethyl)-benzoylamino)-propionic acid tert-butyl ester 6.88 g (14.2 mmol) of tert-butyl (2S)-2-benzyloxycarbonylamino-3-(4-(2-methoxycarbonyl-ethyl)-benzoylamino)propionate was dissolved in 200 ml of methanol and 852 mg (14.2 mmol) of acetic acid was added. The mixture was hydrogenated for 7 hours at room temperature over Pd/C (5% strength) at 1 bar of hydrogen. The mixture was filtered and the solvent was removed in vacuo. The residue was washed with n-heptane and dried in vacuo. Yield 6.9 g. MS (ES$^+$): m/e=351.2 (M+H$^+$).

e) (2S)-3-(4-(2-Methoxycarbonyl-ethyl)-benzoylamino)-2-(naphthalene-1-sulfonylamino)-propionic acid tert-butyl ester 0.123 g (0.35 mmol) of (2S)-2-amino-3-(4-(2-methoxycarbonyl-ethyl)-benzoylamino)-propionic acid tert-butyl ester was dissolved in 2 ml of dimethylformamide and treated with 0.196 ml (1.4 mmol) of triethylamine and 0.159 g (0.7 mmol) of 1-naphthalenesulfonyl chloride. The solution was stirred for 4 hours at room temperature. The solvent was removed in vacuo, the residue was dissolved in dichloromethane and the solution was washed three times with water. The organic phase was dried with sodium sulfate, filtered and the solvent was removed in vacuo. The residue was chromatographed on silica gel eluting with n-heptane/ethyl acetate (1/1). Yield 47 mg. MS (ES$^+$): m/e=541.3 (M+H$^+$).

f) (2S)-2-(Naphthalene-1-sulfonylamino)-3-(4-(2-(1,4,5,6-tetrahydropyrimidin-2-ylcarbamoyl)-ethyl)-benzoylamino)-propionic acid tert-butyl ester 47 mg (0.087 mmol) of (2S)-3-(4-(2-methoxycarbonyl-ethyl)-benzoylamino)-2-(naphthalene-1-sulfonylamino)-propionic acid tert-butyl ester was dissolved in 2 ml of dimethylformamide and 86 mg (0.87 mmol) of 2-amino-1,4,5,6-tetrahydropyrimidine was added. The reaction was stirred at room temperature for 20 hours. The solvent was removed in vacuo and the residue was chromatographed on silica gel eluting with dichloromethane/methanol (1/1), followed by dichloromethane/methanol/acetic acid/water (85/15/1.5/1.5). Yield 46 mg. MS (ES$^+$): m/e=608.3 (M+H$^+$).

g) (2S)-2-(Naphthalene-1-sulfonylamino)-3-(4-(2-(1,4,5,6-tetrahydropyrimidin-2-ylcarbamoyl)-ethyl)-benzoylamino)-propionic acid 45 mg (0.074 mmol) of (2S)-2-(naphthalene-1-sulfonylamino)-3-(4-(2-(1,4,5,6-tetrahydropyrimidin-2-ylcarbamoyl)-ethyl)-benzoylamino)-propionic acid tert-butyl ester was dissolved in 2 ml of dichloromethane and 2 ml of trifluoroacetic acid was added. The solution was stirred at room temperature for 3 hours. The solvent was removed in vacuo and toluene was added to the residue and then removed in vacuo. The residue was dissolved in acetonitrile/water (1/1) and lyophilized. Yield 50 mg. MS (ES$^+$): m/e=552 (M+H$^+$).

Example 2

(2S)-2-(Quinoline-8-sulfonylamino)-3-(4-(2-(1,4,5,6-tetrahydropyrimidin-2-ylcarbamoyl)-ethyl)-benzoylamino)-propionic acid

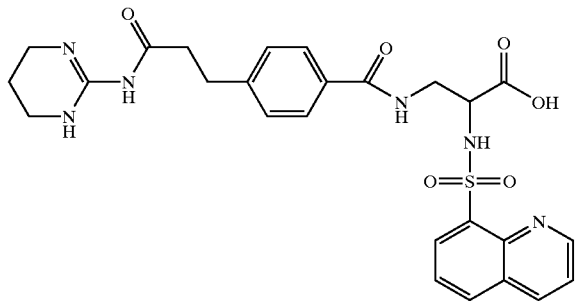

a) (2S)-3-(4-(2-Methoxycarbonyl-ethyl)-benzoylamino)-2-(quinoline-8-sulfonylamino)-propionic acid tert-butyl ester 0.123 g (0.35 mmol) of (2S)-2-amino-3-(4-(2-methoxycarbonyl-ethyl)-benzoylamino)-propionic acid tert-butyl ester was dissolved in 2 ml of dimethylformamide and treated with 0.196 ml (1.4 mmol) of triethylamine and 0.159 g (0.7 mmol) of 8-quinolinesulfonyl chloride. The solution was stirred for 4 hours at room temperature. The solvent was removed in vacuo, the residue was dissolved in dichloromethane and the solution was washed three times with water. The organic phase was dried with sodium sulfate, filtered and the solvent was removed in vacuo. The residue was chromatographed on silica gel eluting with n-heptane/ethyl acetate (1/1). Yield 67 mg. MS (ES$^+$): m/e=542.2 (M+H$^+$).

b) (2S)-2-(Quinoline-8-sulfonylamino)-3-(4-(2-(1,4,5,6-tetrahydropyrimidin-2-ylcarbamoyl)-ethyl)-benzoylamino)-propionic acid tert-butyl ester 65 mg (0.12 mmol) of (2S)-3-(4-(2-methoxycarbonyl-ethyl)-benzoylamino)-2-(quinoline-8-sulfonylamino)-propionic acid tert-butyl ester was dissolved in 1 ml of dimethylformamide and 59 mg (0.6 mmol) of 2-amino-1,4, 5,6-tetrahydropyrimidine was added. The reaction was stirred at room temperature for 20 hours. The solvent was removed in vacuo and the residue was chromatographed on silica gel eluting with dichloromethane/methanol (1/1), followed by dichloromethane/methanol/acetic acid/water (85/15/1.5/1.5). Yield 72 mg. MS (ES$^+$): m/e=609.3 (M+H$^+$).

c) (2S)-2-(Quinoline-8-sulfonylamino)-3-(4-(2-(1,4,5,6-tetrahydropyrimidin-2-ylcarbamoyl)-ethyl)-benzoylamino)-propionic acid 72 mg (0.11 mmol) of (2S)-2-(quinoline-8-sulfonylamino)-3-(4-(2-(1,4,5,6-tetrahydropyrimidin-2-ylcarbamoyl)-ethyl)-benzoylamino)-propionic acid tert-butyl ester was dissolved in 2 ml of dichloromethane and 2 ml of trifluoroacetic acid was added. The solution was stirred at room temperature for 3 hours. The solvent was removed in vacuo and toluene was added to the residue and then removed in vacuo. The residue was dissolved in acetonitrile/water (1/1) and lyophilized. Yield 54 mg. MS (ES$^+$): m/e=553 (M+H$^+$).

Example 3

(2S)-2-(4-Acetylamino-benzenesulfonylamino)-3-(4-(2-(1,4,5,6-tetrahydropyrimidin-2- ylcarbamoyl)-ethyl)-benzoylamino)-propionic acid

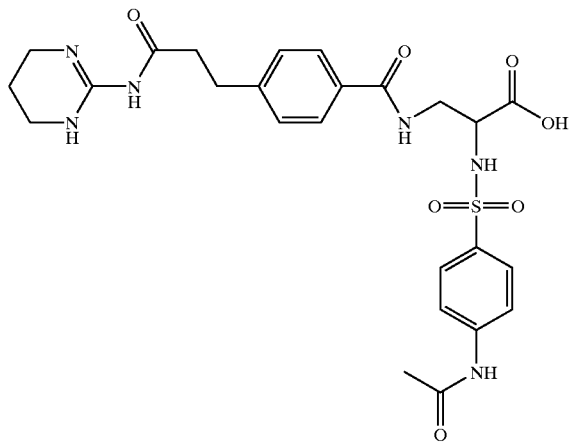

a) (2S)-2-(4-Acetylamino-benzenesulfonylamino)-3-(4-(2-methoxycarbonyl-ethyl)-benzoylamino)-propionic acid tert-butyl ester 0.123 g (0.35 mmol) of (2S)-2-amino-3-(4-(2-methoxycarbonyl-ethyl)-benzoylamino)-propionic acid tert-butyl ester was dissolved in 2 ml of dimethylformamide and treated with 0.196 ml (1.4 mmol) of triethylamine and 0.164 g (0.7 mmol) of 4-acetylamino-benzenesulfonyl chloride. The solution was stirred for 4 hours at room temperature. The solvent was removed in vacuo, the residue was dissolved in dichloromethane and the solution was washed three times with water. The organic phase was dried with sodium sulfate, filtered and the solvent was removed in vacuo. The residue was chromatographed on silica gel eluting with n-heptane/ethyl acetate (1/2). Yield 90 mg. MS (ES$^+$): m/e=548 (M+H$^+$).

b) (2S)-2-(4-Acetylamino-benzenesulfonylamino)-3-(4-(2-(1,4,5,6-tetrahydropyrimidin-2-ylcarbamoyl)-ethyl)-benzoylamino)-propionic acid tert-butyl ester 87 mg (0.16 mmol) of (2S)-2-(4-acetylamino-benzenesulfonylamino)-3-(4-(2-methoxycarbonyl-ethyl)-benzoylamino)-propionic acid tert-butyl ester was dissolved in 1 ml of dimethylformamide and 79 mg (0.8 mmol) of 2-amino-1,4,5,6-tetrahydropyrimidine was added. The reaction was stirred at room temperature for 20 hours. The solvent was removed in vacuo and the residue was chromatographed on silica gel eluting with dichloromethane/methanol (1/1), followed by dichloromethane/methanol/acetic acid/water (85/15/1.5/1.5). Yield 57 mg. MS (ES$^+$): m/e=615.3 (M+H$^+$).

c) (2S)-2-(4-Acetylamino-benzenesulfonylamino)-3-(4-(2-(1,4,5,6-tetrahydropyrimidin-2-ylcarbamoyl)-ethyl)-benzoylamino)-propionic acid 57 mg (0.09 mmol) of (2S)-2-(4-acetylamino-benzenesulfonylamino)-3-(4-(2-(1,4,5,6-tetrahydropyrimidin-2-ylcarbamoyl)-ethyl)-benzoylamino)-propionic acid tert-butyl ester was dissolved in 2 ml of dichloromethane and 2 ml of trifluoroacetic acid was added. The solution was stirred at room temperature for 3 hours. The solvent was removed in vacuo and toluene was added to the residue and then removed in vacuo. The residue was dissolved in acetonitrile/water (1/1) and lyophilized. Yield 42 mg. MS (ES$^+$): m/e=559.2 (M+H$^+$).

Example 4

(2S)-2-(2-(1,4,5,6-Tetrahydropyrimidin-2-ylcarbamoyl)-benzenesulfonylamino)-3-(4-(2-(1,4,5, 6-tetrahydropyrimidin-2-ylcarbamoyl)-ethyl)-benzoylamino)-propionic acid

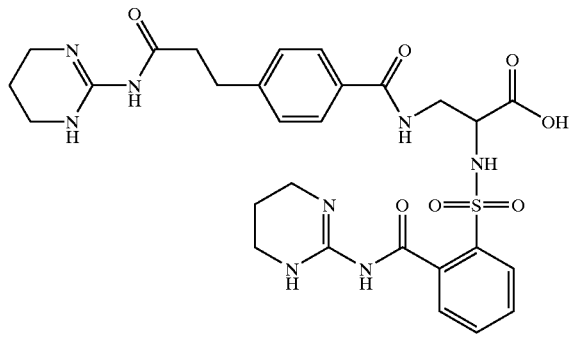

a) 2-((1 S)-1-tert-Butoxycarbonyl-2-(4-(2-methoxycarbonyl-ethyl)-benzoylamino)-ethylsulfamoyl)-benzoic acid methyl ester 0.123 g (0.35 mmol) of (2S)-2-amino-3-(4-(2-methoxycarbonyl-ethyl)-benzoylamino)-propionic acid tert-butyl ester was dissolved in 2 ml of dimethylformamide and treated with 0.196 ml (1.4 mmol) of triethylamine and 0.164 g (0.7 mmol) of 2-(methoxycarbonyl)-benzenesulfonyl chloride. The solution was stirred for 4 hours at room temperature. The solvent was removed in vacuo, the residue was dissolved in dichloromethane and the solution was washed three times with water. The organic phase was dried with sodium sulfate, filtered and the solvent was removed in vacuo. The residue was chromatographed on silica gel eluting with n-heptane/ethyl acetate (1/1). Yield 75 mg. MS (ES$^+$): m/e=549 (M+H$^+$).

b) (2S)-2-(2-(1,4,5,6-Tetrahydropyrimidin-2-ylcarbamoyl)-benzenesulfonylamino)-3-(4-(2-(1,4,5,6-tetrahydropyrimidin-2-ylcarbamoyl)-ethyl)-benzoylamino)-propionic acid tert-butyl ester 75 mg (0.13 mmol) of 2-((1S)-1-tert-butoxycarbonyl-2-(4-(2-methoxycarbonyl-ethyl)-benzoylamino)-ethylsulfamoyl)-benzoic acid methyl ester was dissolved in 1 ml of dimethylformamide and 68 mg (0.69 mmol) of 2-amino-1,4,5,6-tetrahydropyrimidine was added. The reaction was stirred at room temperature for 20 hours. The solvent was removed in vacuo and the residue was chromatographed on silica gel eluting with dichloromethane/methanol (1/1), followed by dichloromethane/methanol/acetic acid/water (85/15/1.5/1.5). Yield 54 mg. MS (ES$^+$): m/e=683.3 (M+H$^+$).

c) (2S)-2-(2-(1,4,5,6-Tetrahydropyrimidin-2-ylcarbamoyl)-benzenesulfonylamino)-3-(4-(2-(1,4,5,6-tetrahydropyrimidin-2-ylcarbamoyl)-ethyl)-benzoylamino)-propionic acid 54 mg (0.08 mmol) of (2S)-2-(2-(1,4,5,6-tetrahydropyrimidin-2-ylcarbamoyl)-benzenesulfonylamino)-3-(4-(2-(1,4,5,6-tetrahydropyrimidin-2-ylcarbamoyl)-ethyl)-benzoylamino)-propionic acid tert-butyl ester was dissolved in 2 ml of dichloromethane and 2 ml of trifluoroacetic acid was added. The solution was stirred at room temperature for 3 hours. The solvent was removed in vacuo and toluene was added to the residue and then removed in vacuo. The residue was dissolved in acetonitrile/water (1/1) and lyophilized. Yield 34 mg. MS (ES$^+$): m/e=627 (M+H$^+$).

General Procedure 1 (Synthesis of the Compounds of Examples 5 to 24)

Step a: Reaction with the Sulfonyl Chloride 0.2 g of (2S)-2-amino-3-(4-(2-methoxycarbonyl-ethyl)-benzoylamino)-propionic acid tert-butyl ester was dissolved in 2 ml of dimethylformamide and treated with 4 molar equivalents of triethylamine and 2 molar equivalents of the appropriate sulfonyl chloride. The solution was stirred for 4 hours at room temperature. The solvent was removed in vacuo, the residue was dissolved in dichloromethane and the solution was washed three times with water. The organic phase was dried with sodium sulfate, filtered and the solvent was removed in vacuo. The residue was chromatographed on silica gel eluting with n-heptane/ethyl acetate (1/1).

Step b: Formation of the Acyl Guanidine

The product of step a was dissolved in 1 ml of dimethylformamide and 5 molar equivalents of 2-amino-1,4,5,6-tetrahydropyrimidine was added. The reaction mixture was stirred at room temperature for 20 hours. The solvent was removed in vacuo and the residue was chromatographed on silica gel eluting with dichloromethane/methanol (1/1), followed by dichloromethane/methanol/acetic acid/water (85/15/1.5/1.5).

Step c: Cleavage of the Tert-butyl Ester

The product of step b was dissolved in 2 ml of dichloromethane and 2 ml of trifluoroacetic acid was added. The solution was stirred at room temperature for 3 hours. The solvent was removed in vacuo, and toluene was added to the residue and then removed in vacuo. The residue was dissolved in acetonitrile/water (1/1) and lyophilized.

Example 5

(2S)-2-(4-tert-Butyl-benzenesulfonylamino)-3-(4-(2-(1,4,5,6-tetrahydropyrimidin-2-ylcarbamoyl)-ethyl)-benzoylamino)-propionic acid

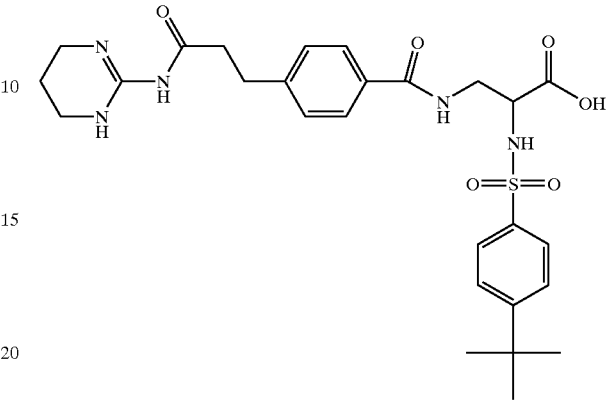

The title compound was synthesized according to general procedure 1, using 4-tert-butyl-benzenesulfonyl chloride in step a.

|  | Yield | MS (ES$^+$): m/e |
|---|---|---|
| Product of step a | 83 mg | 547.2 (M + H)$^+$ |
| Product of step b | 85 mg | 614.3 (M + H)$^+$ |
| Product of step c (title compound) | 75 mg | 558.3 (M + H)$^+$ |

Example 6

(2S)-2-(Propane-1-sulfonylamino)-3-(4-(2-(1,4,5,6-tetrahydropyrimidin-2-ylcarbamoyl)-ethyl)-benzoylamino)-propionic acid

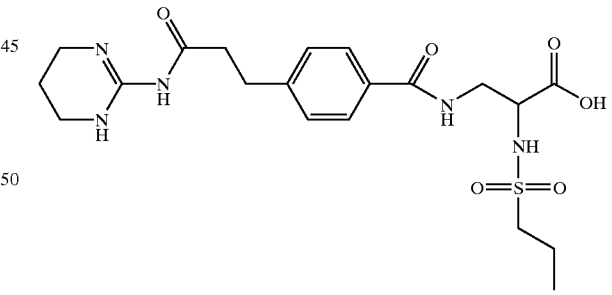

The title compound was synthesized according to general procedure 1, using propane-1-sulfonyl chloride in step a.

|  | Yield | MS (ES$^+$): m/e |
|---|---|---|
| Product of step a | 54 mg | 457.3 (M + H)$^+$ |
| Product of step b | 55 mg | 524.3 (M + H)$^+$ |
| Product of step c (title compound) | 45 mg | 468.3 (M + H)$^+$ |

Example 7

(2S)-2-(2-Phenyl-ethenesulfonylamino)-3-(4-(2-(1,4,5,6-tetrahydropyrimidin-2-ylcarbamoyl)-ethyl)-benzoylamino)-propionic acid

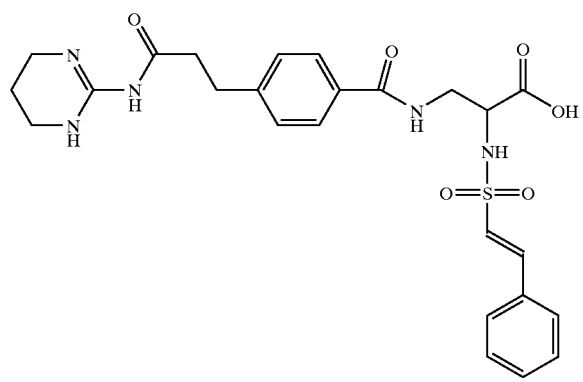

The title compound was synthesized according to general procedure 1, using trans-beta-styrenesulfonyl chloride in step a.

|  | Yield | MS (ES+): m/e |
|---|---|---|
| Product of step a | 49 mg | 517.1 (M + H)+ |
| Product of step b | 45 mg | 584.3 (M + H)+ |
| Product of step c (title compound) | 37 mg | 528.3 (M + H)+ |

Example 8

(2S)-2-(4-Propyl-benzenesulfonylamino)-3-(4-(2-(1,4,5,6-tetrahydropyrimidin-2-ylcarbamoyl)-ethyl)-benzoylamino)-propionic acid

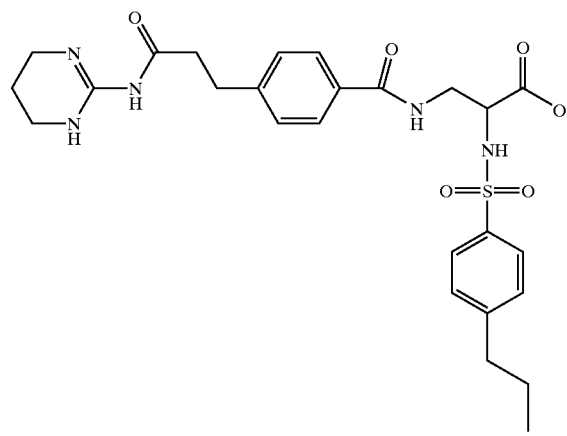

The title compound was synthesized according to general procedure 1, using 4-(n-propyl)-benzenesulfonyl chloride in step a.

|  | Yield | MS (ES+): m/e |
|---|---|---|
| Product of step a | 78 mg | 533.2 (M + H)+ |
| Product of step b | 73 mg | 600.4 (M + H)+ |
| Product of step c (title compound) | 55 mg | 544.3 (M + H)+ |

Example 9

(2S)-2-(2-Methyl-propane-1-sulfonylamino)-3-(4-(2-(1,4,5,6-tetrahydropyrimidin-2-ylcarbamoyl)-ethyl)-benzoylamino)-propionic acid

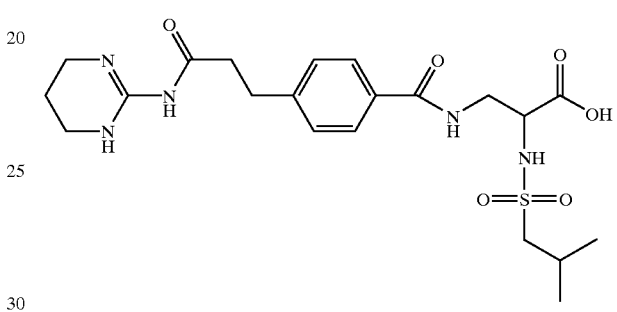

The title compound was synthesized according to general procedure 1, using 2-methyl-propane-1-sulfonyl chloride in step a.

|  | Yield | MS (ES+): m/e |
|---|---|---|
| Product of step a | 21 mg | 471.3 (M + H)+ |
| Product of step b | 10 mg | 538.4 (M + H)+ |
| Product of step c (title compound) | 13 mg | 482.3 (M + H)+ |

Example 10

(2S)-2-(4-Butoxy-benzenesulfonylamino)-3-(4-(2-(1,4,5,6-tetrahydropyrimidin-2-ylcarbamoyl)-ethyl)-benzoylamino)-propionic acid

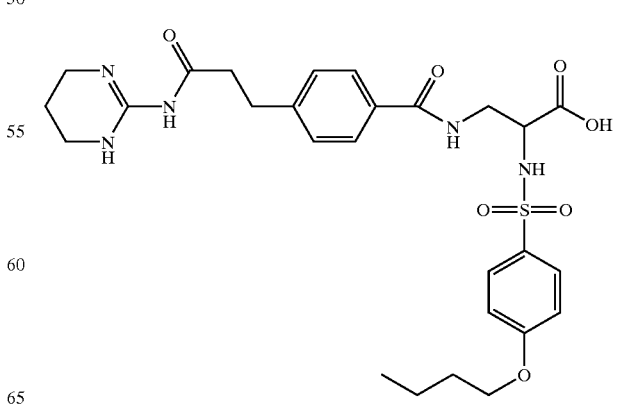

The title compound was synthesized according to general procedure 1, using 4-(n-butoxy)-benzenesulfonyl chloride in step a.

|  | Yield | MS (ES$^+$): m/e |
|---|---|---|
| Product of step a | 83 mg | 563.2 (M + H)$^+$ |
| Product of step b | 83 mg | 630.4 (M + H)$^+$ |
| Product of step c (title compound) | 63 mg | 574.3 (M + H)$^+$ |

Example 11

(2S)-2-(2-Cyano-benzenesulfonylamino)-3-(4-(2-(1,4,5,6-tetrahydropyrimidin-2-ylcarbamoyl)-ethyl)-benzoylamino)-propionic acid

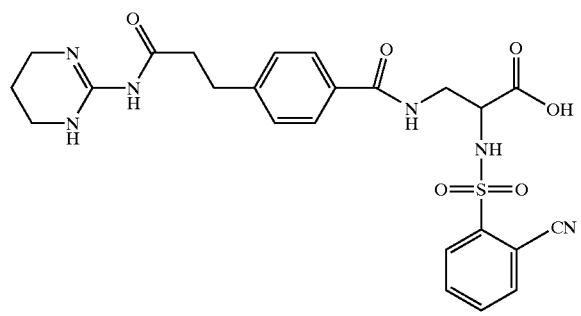

The title compound was synthesized according to general procedure 1, using 2-cyano-benzenesulfonyl chloride in step a.

|  | Yield | MS (ES$^+$): m/e |
|---|---|---|
| Product of step a | 91 mg | 516.2 (M + H)$^+$ |
| Product of step b | 71 mg | 583.3 (M + H)$^+$ |
| Product of step c (title compound) | 73 mg | 527.3 (M + H)$^+$ |

Example 12

(2S)-2-(7,7-Dimethyl-2-oxo-bicyclo[2.2.1]hept-1-ylmethanesulfonylamino)-3-(4-(2-(1,4,5,6-tetrahydropyrimidin-2-ylcarbamoyl)-ethyl)-benzoylamino)-propionic acid

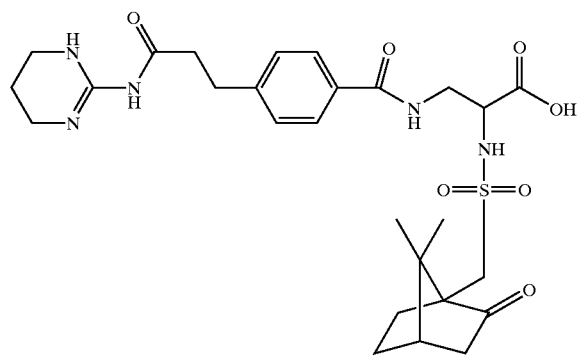

The title compound was synthesized according to general procedure 1, using 10-camphorsulfonyl chloride in step a.

|  | Yield | MS (ES$^+$): m/e |
|---|---|---|
| Product of step a | 85 mg | 565.3 (M + H)$^+$ |
| Product of step b | 88 mg | 632.4 (M + H)$^+$ |
| Product of step c (title compound) | 71 mg | 576.4 (M + H)$^+$ |

Example 13

(2S)-2-(4-Chloro-benzenesulfonylamino)-3-(4-(2-(1,4,5,6-tetrahydropyrimidin-2-ylcarbamoyl)-ethyl)-benzoylamino)-propionic acid

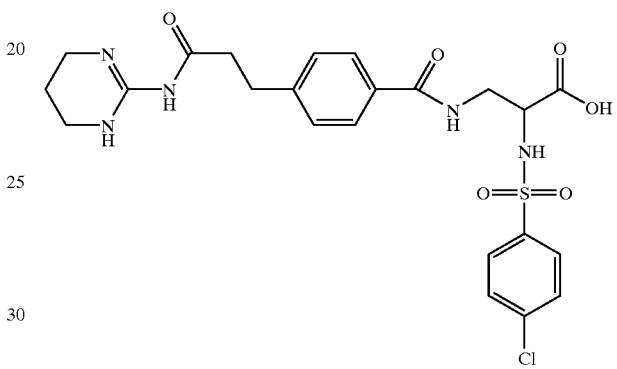

The title compound was synthesized according to general procedure 1, using 4-chloro-benzenesulfonyl chloride in step a.

|  | Yield | MS (ES$^+$): m/e |
|---|---|---|
| Product of step a | 91 mg | 525.1 (M + H)$^+$ |
| Product of step b | 82 mg | 592.3 (M + H)$^+$ |
| Product of step c (title compound) | 64 mg | 536.3 (M + H)$^+$ |

Example 14

(2S)-2-(3-Chloro-benzenesulfonylamino)-3-(4-(2-(1,4,5,6-tetrahydropyrimidin-2-ylcarbamoyl)-ethyl)-benzoylamino)-propionic acid

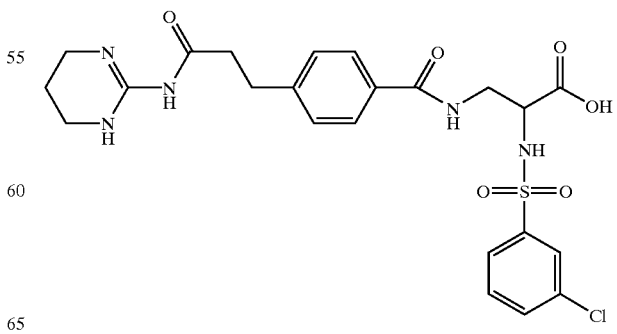

The title compound was synthesized according to general procedure 1, using 3-chloro-benzenesulfonyl chloride in step a.

|  | Yield | MS (ES⁺): m/e |
|---|---|---|
| Product of step a | 65 mg | 525.2 (M + H)⁺ |
| Product of step b | 58 mg | 592.3 (M + H)⁺ |
| Product of step c (title compound) | 52 mg | 536.3 (M + H)⁺ |

Example 15

(2S)-3-(4-(2-(1,4,5,6-Tetrahydropyrimidin-2-ylcarbamoyl)-ethyl)-benzoylamino)-2-(3-trifluoromethyl-benzenesulfonylamino)-propionic acid

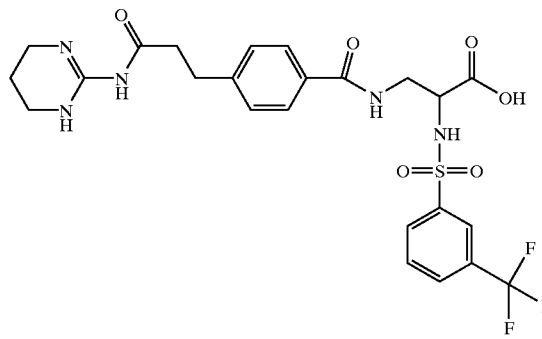

The title compound was synthesized according to general procedure 1, using 3-trifluoromethyl-benzenesulfonyl chloride in step a.

|  | Yield | MS (ES⁺): m/e |
|---|---|---|
| Product of step a | 86 mg | 559.2 (M + H)⁺ |
| Product of step b | 94 mg | 626.3 (M + H)⁺ |
| Product of step c (title compound) | 84 mg | 570.3 (M + H)⁺ |

Example 16

(2S)-2-(4-Methoxy-benzenesulfonylamino)-3-(4-(2-(1,4,5,6-tetrahydropyrimidin-2-ylcarbamoyl)-ethyl)-benzoylamino)-propionic acid

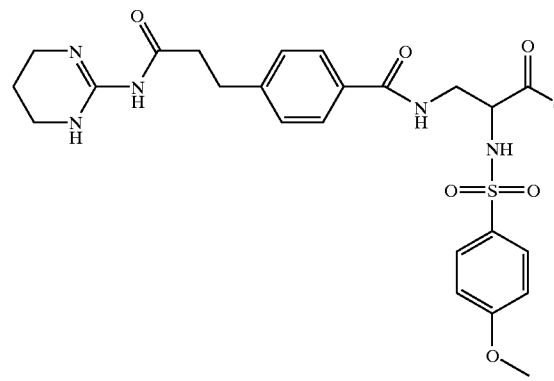

The title compound was synthesized according to general procedure 1, using 4-methoxy-benzenesulfonyl chloride in step a.

|  | Yield | MS (ES⁺): m/e |
|---|---|---|
| Product of step a | 66 mg | 521.1 (M + H)⁺ |
| Product of step b | 71 mg | 588.3 (M + H)⁺ |
| Product of step c (title compound) | 49 mg | 532.3 (M + H)⁺ |

Example 17

(2S)-2-Benzenesulfonylamino-3-(4-(2-(1,4,5,6-tetrahydropyrimidin-2-ylcarbamoyl)-ethyl)-benzoylamino)-propionic acid

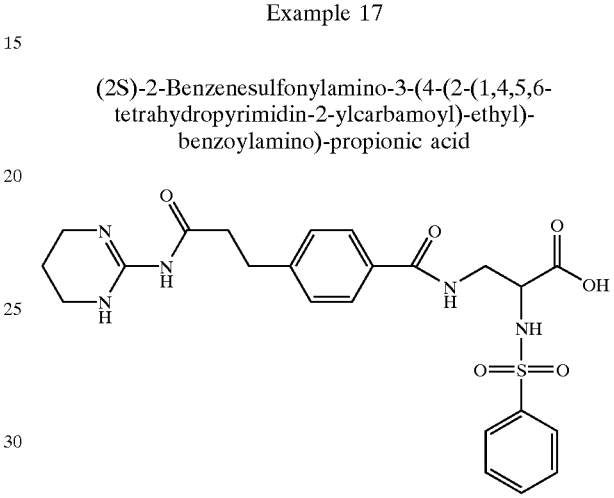

The title compound was synthesized according to general procedure 1, using benzenesulfonyl chloride in step a.

|  | Yield | MS (ES⁺): m/e |
|---|---|---|
| Product of step a | 76 mg | 491.2 (M + H)⁺ |
| Product of step b | 77 mg | 558.3 (M + H)⁺ |
| Product of step c (title compound) | 64 mg | 502.3 (M + H)⁺ |

Example 18

(2S)-3-(4-(2-(1,4,5,6-Tetrahydropyrimidin-2-ylcarbamoyl)-ethyl)-benzoylamino)-2-(thiophene-2-sulfonylamino)-propionic acid

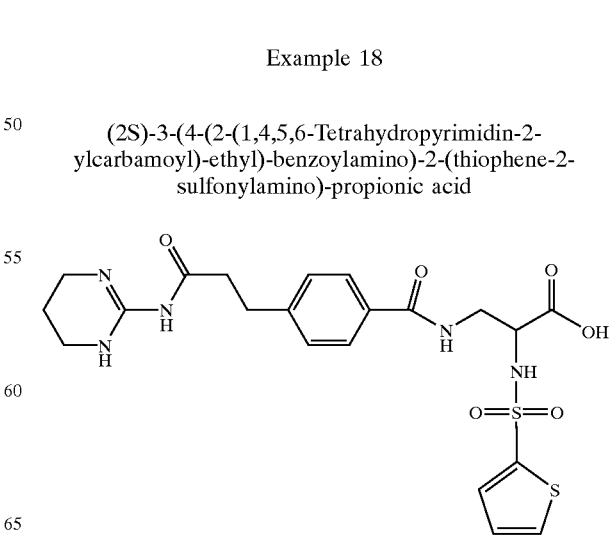

The title compound was synthesized according to general procedure 1, using 2-thiophenesulfonyl chloride in step a.

|  | Yield | MS (ES+): m/e |
|---|---|---|
| Product of step a | 87 mg | 497.1 (M + H)+ |
| Product of step b | 74 mg | 564.2 (M + H)+ |
| Product of step c (title compound) | 64 mg | 508.2 (M + H)+ |

Example 19

(2S)-2-(Biphenyl-4-sulfonylamino)-3-(4-(2-(1,4,5,6-tetrahydropyrimidin-2-ylcarbamoyl)-ethyl)-benzoylamino)-propionic acid

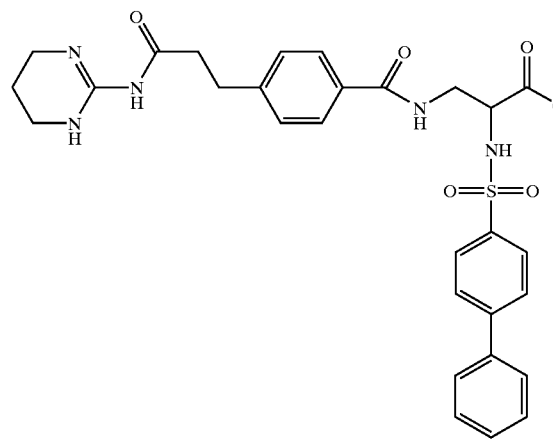

The title compound was synthesized according to general procedure 1, using 4-biphenylsulfonyl chloride in step a.

|  | Yield | MS (ES+): m/e |
|---|---|---|
| Product of step a | 39 mg | 567.1 (M + H)+ |
| Product of step b | 40 mg | 634.4 (M + H)+ |
| Product of step c (title compound) | 33 mg | 578.3 (M + H)+ |

Example 20

(2S)-2-(Naphthalene-2-sulfonylamino)-3-(4-(2-(1,4,5,6-tetrahydropyrimidin-2-ylcarbamoyl)-ethyl)-benzoylamino)-propionic acid

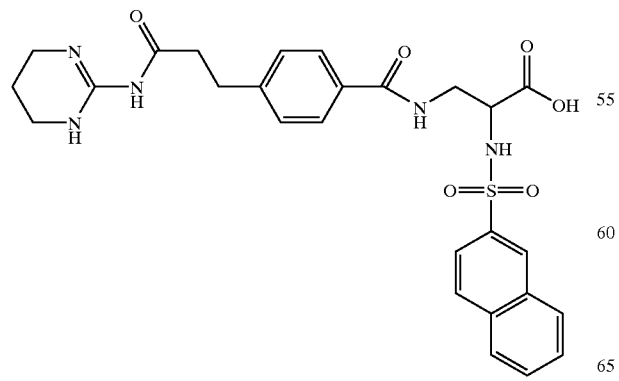

The title compound was synthesized according to general procedure 1, using 2-naphthalenesulfonyl chloride in step a.

|  | Yield | MS (ES+): m/e |
|---|---|---|
| Product of step a | 76 mg | 541.2 (M + H)+ |
| Productof step b | 74 mg | 608.3 (M + H)+ |
| Product of step c (title compound) | 62 mg | 552.3 (M + H)+ |

Example 21

(2S)-3-(4-(2-(1,4,5,6-Tetrahydropyrimidin-2-ylcarbamoyl)-ethyl)-benzoylamino)-2-(2,4,6-trimethyl-benzenesulfonylamino)-propionic acid

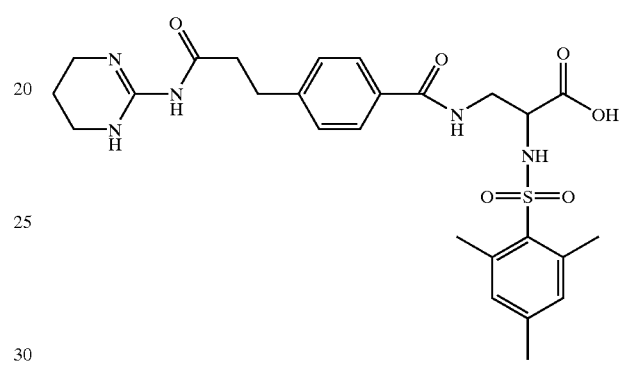

The title compound was synthesized according to general procedure 1, using 2,4,6-trimethylbenzenesulfonyl chloride in step a.

|  | Yield | MS (ES+): m/e |
|---|---|---|
| Product of step a | 68 mg | 533.2 (M + H)+ |
| Product of step b | 71 mg | 600.4 (M + H)+ |
| Product of step c (title compound) | 54 mg | 544.3 (M + H)+ |

Example 22

(2S)-3-(4-(2-(1,4,5,6-Tetrahydropyrimidin-2-ylcarbamoyl)-ethyl)-benzoylamino)-2-(4-trifluoromethyl-benzenesulfonylamino)-propionic acid

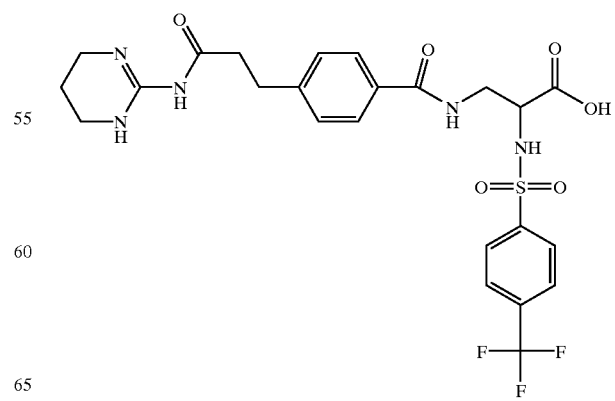

The title compound was synthesized according to general procedure 1, using 4-trifluoromethyl-benzenesulfonyl chloride in step a.

|  | Yield | MS (ES+): m/e |
|---|---|---|
| Product of step a | 105 mg | 559.3 (M + H)+ |
| Product of step b | 93 mg | 626.4 (M + H)+ |
| Product of step c (title compound) | 70 mg | 570.3 (M + H)+ |

Example 23

(2S)-2-(Butane-1-sulfonylamino)-3-(4-(2-(1,4,5,6-tetrahydropyrimidin-2-ylcarbamoyl)-ethyl)-benzoylamino)-propionic acid

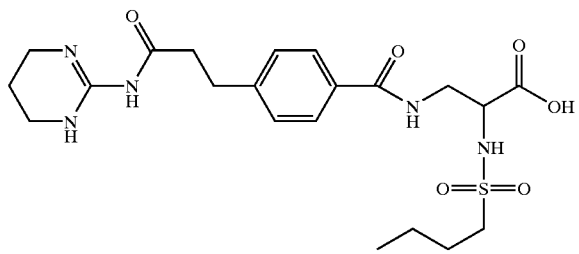

The title compound was synthesized according to general procedure 1, using butane-1-sulfonyl chloride in step a.

|  | Yield | MS (ES+): m/e |
|---|---|---|
| Product of step a | 87 mg | 471.4 (M + H)+ |
| Product of step b | 60 mg | 538.4 (M + H)+ |
| Product of step c (title compound) | 57 mg | 482.3 (M + H)+ |

Example 24

(2S)-2-Methanesulfonylamino-3-(4-(2-(1,4,5,6-tetrahydropyrimidin-2-ylcarbamoyl)-ethyl)-benzoylamino)-propionic acid

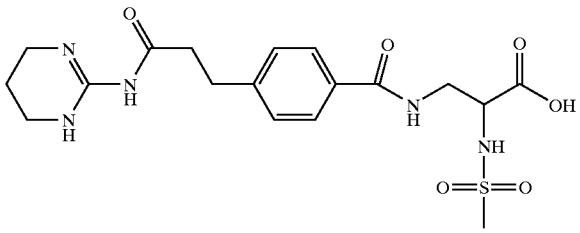

The title compound was synthesized according to general procedure 1, using methanesulfonyl chloride in step a.

|  | Yield | MS (ES+): m/e |
|---|---|---|
| Product of step a | 87.8 mg | 429.3 (M + H)+ |
| Product of step b | 98 mg | 496.4 (M + H)+ |
| Product of step c (title compound) | 74 mg | 440.3 (M + H)+ |

General Procedure 2 (Synthesis of the Compounds of Examples 25 to 27)

Step a: Reaction with the Sulfonyl Chloride 0.1 g of (2S)-2-amino-3-(4-(2-carboxy-ethyl)-benzoylamino)-propionic acid tert-butyl ester hydrochloride was dissolved in 3 ml of dimethylformamide and treated with 3 molar equivalents of diisopropylethylamine and 2 molar equivalents of the appropriate sulfonyl chloride at 0° C. The solution was stirred for 3 hours at 0° C. The reaction mixture was diluted by the addition of ethyl acetate and the solution was washed twice with aqueous potassium hydrogensulfate solution and once with saturated aqueous sodium chloride solution. The organic phase was dried with magnesium sulfate, filtered and the solvent was removed in vacuo. The residue was chromatographed on silica gel eluting with dichloromethane/methanol/acetic acid/water (97.5/2.5/0.25/0.25).

Step b: Formation of the Acyl Guanidine

The product of step a was dissolved in 2 ml of tetrahydrofuran and 1.2 molar equivalents of 2-amino-1,4,5,6-tetrahydropyrimidine, 4 molar equivalents of diisopropylethylamine, and 1.1 molar equivalents of O-(7azabenzotriazol-1-yl)-1,1,3,3-tetramethyluronium hexafluorophosphate were added. The reaction was stirred at room temperature for 20 hours. The solvent was removed in vacuo and the residue was dissolved in ethyl acetate and the solution was washed twice with saturated aqueous sodium bicarbonate solution and once with saturated aqueous sodium chloride solution. The organic phase was dried with magnesium sulfate, filtered and the solvent was removed in vacuo. The residue was chromatographed on silica gel eluting with dichloromethane/methanol/acetic acid/water (85/15/1.5/1.5) followed by dichloromethane/methanol/acetic acid/water (9/1/0.1/0.1).

Step c: Cleavage of the Tert-butyl Ester

The product of step b was dissolved in 1.5 ml of trifluoroacetic acid/water (95/5). The solution was stirred at room temperature for 1 hour. The solvent was removed in vacuo and toluene was added to the residue and then removed in vacuo. The residue was dissolved in acetonitrile/water (1/1) and lyophilized.

Example 25

(2S)-2-(Propane-2-sulfonylamino)-3-(4-(2-(1,4,5,6-tetrahydropyrimidin-2-ylcarbamoyl)-ethyl)-benzoylamino)-propionic acid

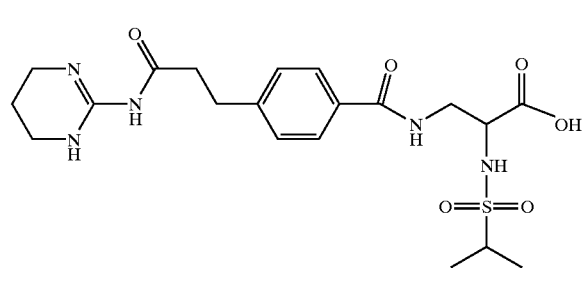

The title compound was synthesized according to general procedure 2, using propane-2-sulfonyl chloride in step a.

|  | Yield | MS: m/e |
|---|---|---|
| Product of step a | 17 mg | 443.2 (M + H)+ (FAB+) |
| Product of step b | 7 mg | 524.2 (M + H)+ (ES+) |
| Product of step c (title compound) | 7.2 mg | 468.2 (M + H)+ (ES+) |

Example 26

(2S)-2-Chloromethanesulfonylamino-3-(4-(2-(1,4,5,6-tetrahydropyrimidin-2-ylcarbamoyl)-ethyl)-benzoylamino)-propionic acid

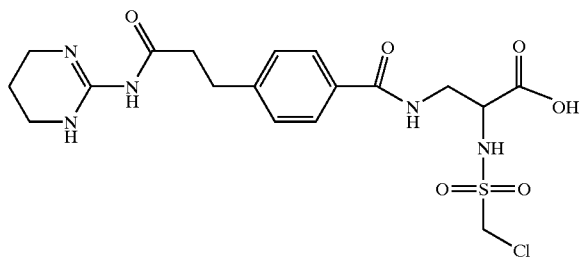

The title compound was synthesized according to general procedure 2, using chloromethanesulfonyl chloride in step a.

|  | Yield | MS: m/e |
|---|---|---|
| Product of step a | 94 mg | 449.1 (M + H)+ (FAB+) |
| Product of step b | 28 mg | 530.2 (M)+(ES+) |
| Product of step c (title compound) | 34 mg | 474.2 (M + H)+ (ES+) |

Example 27

(2S)-3-(4-(2-(1,4,5,6-Tetrahydropyrimidin-2-ylcarbamoyl)-ethyl)-benzoylamino)-2-(2,2,2-trifluoro-ethanesulfonylamino)-propionic acid

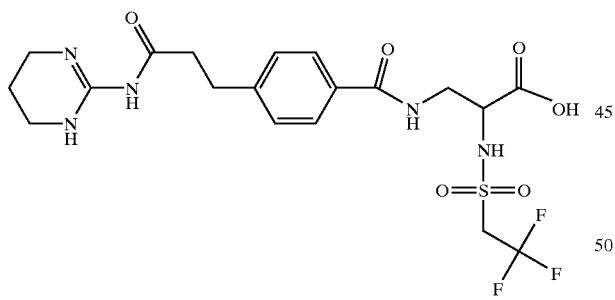

The title compound was synthesized according to general procedure 2, using 2,2,2-trifluoroethanesulfonyl chloride in step a.

|  | Yield | MS: m/e |
|---|---|---|
| Product of step a | 43 mg | 483.2 (M + H)+ (FAB+) |
| Product of step b | 24 mg | 564.2 (M + H)+ (ES+) |
| Product of step c (title compound) | 22 mg | 508.2 (M + H)+ (ES+) |

Example 28

(2S)-2-(4-tert-Butyl-benzenesulfonylamino)-3-(4-(2-(1,4,5,6-tetrahydropyrimidin-2-ylcarbamoyl)-ethyl)-benzoylamino)-propionic acid ethyl ester

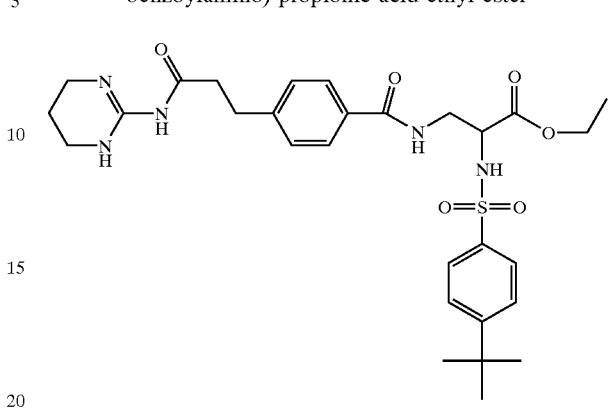

700 mg of (2S)-2-(4-tert-butyl-benzenesulfonylamino)-3-(4-(2-(1,4,5,6-tetrahydropyrimidin-2-ylcarbamoyl)-ethyl)-benzoylamino)-propionic acid was dissolved in 100 ml of ethanol and 15 drops of concentrated sulfuric acid was added. The reaction solution was boiled for 3.5 hours. The solvent was removed in vacuo, the residue was dissolved in dichloromethane and washed three times with saturated aqueous sodium bicarbonate solution. The aqueous phase was extracted once with dichloromethane and the combined organic phase was washed twice with saturated aqueous sodium chloride solution. The organic phase was dried with sodium sulfate, filtered and the solvent was removed in vacuo. The residue was dissolved in 2N aqueous hydrochloric acid. The hydrochloric acid was removed in vacuo, the residue was dissolved in acetonitrile and added to water. This mixture was lyophilized. Yield 480 mg. MS (ES+): m/e=586.4 (M+H)+.

Example 29

(2S)-2-(4-tert-Butyl-benzenesulfonylamino)-3-(4-(2-(1,4,5,6-tetrahydropyrimidin-2-ylcarbamoyl)-ethyl)-benzoylamino)-propionic acid isopropyl ester

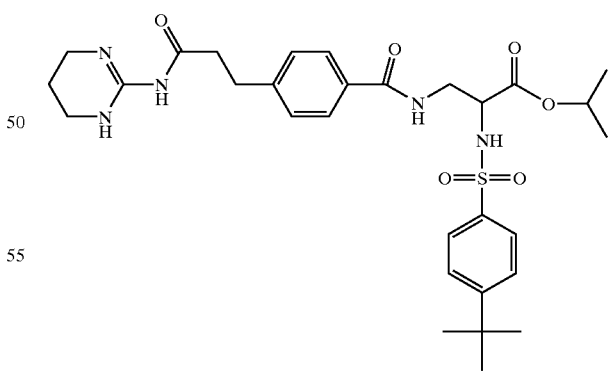

700 mg of (2S)-2-(4-tert-butyl-benzenesulfonylamino)-3-(4-(2-(1,4,5,6-tetrahydropyrimidin-2-ylcarbamoyl)-ethyl)-benzoylamino)-propionic acid was dissolved in 100 ml of isopropanol and 15 drops of concentrated sulfuric acid was added. The reaction solution was boiled for 2.5 days. The solvent was removed in vacuo, the residue was dissolved in dichloromethane and washed three times with saturated aqueous sodium bicarbonate solution. The aqueous phase was extracted once with dichloromethane and the combined organic phase was washed twice with saturated aqueous sodium chloride solution. The organic phase was dried with sodium sulfate, filtered and the solvent was removed in vacuo. The residue was dissolved in 2N aqueous hydrochloric acid. The hydrochloric acid was removed in vacuo, the residue was dissolved in acetonitrile and added to water. This mixture was lyophilized. Yield 444 mg. MS (ES$^+$): m/e=600.4 (M+H)$^+$.

Example 30

(2S)-2-(Naphthalene-1-sulfonylamino)-3-(4-(2-(1,4,5,6-tetrahydropyrimidin-2-ylcarbamoyl)-ethyl)-benzoylamino)-propionic acid ethyl ester

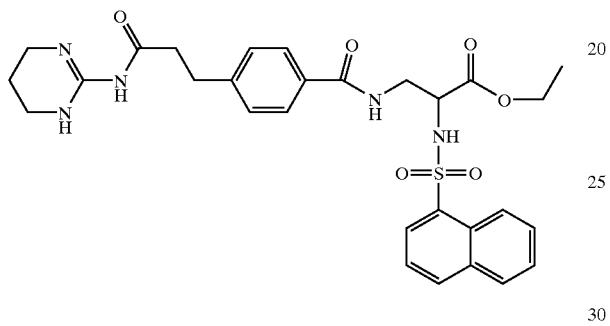

590 mg of (2S)-2-(naphthalene-1-sulfonylamino)-3-(4-(2-(1,4,5,6-tetrahydropyrimidin-2-ylcarbamoyl)-ethyl)-benzoylamino)-propionic acid was dissolved in 80 ml of ethanol and 12 drops of concentrated sulfuric acid was added. The reaction solution was boiled for 3 hours. The solvent was removed in vacuo, the residue was dissolved in dichloromethane and washed three times with saturated aqueous sodium bicarbonate solution. The aqueous phase was extracted once with dichloromethane and the combined organic phase was washed twice with saturated aqueous sodium chloride solution. The organic phase was dried with sodium sulfate, filtered and the solvent was removed in vacuo. The residue was dissolved in 2N aqueous hydrochloric acid. The hydrochloric acid was removed in vacuo, the residue was dissolved in acetonitrile and added to water. This mixture was lyophilized. Yield 381 mg. MS (ES$^+$): m/e=580.3 (M+H)$^+$.

Example 31

(2S)-2-(Naphthalene-1-sulfonylamino)-3-(4-(2-(1,4,5,6-tetrahydropyrimidin-2-ylcarbamoyl)-ethyl)-benzoylamino)-propionic acid isopropyl ester

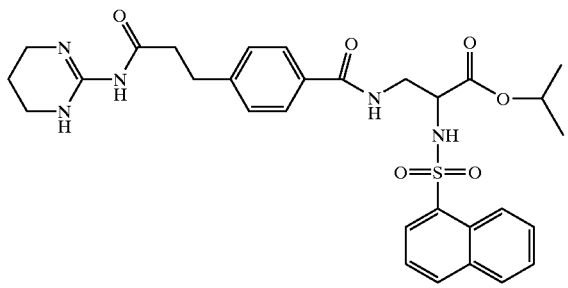

1.5 g of (2S)-2-(naphthalene-1-sulfonylamino)-3-(4-(2-(1,4,5,6-tetrahydropyrimidin-2-ylcarbamoyl)-ethyl)-benzoylamino)-propionic acid was dissolved in 250 ml of isopropanol and 1 ml of concentrated sulfuric acid was added. The reaction solution was boiled for 3 days. The solvent was removed in vacuo, the residue was dissolved in dichloromethane and washed three times with saturated aqueous sodium bicarbonate solution. The aqueous phase was extracted once with dichloromethane and the combined organic phase was washed twice with saturated aqueous sodium chloride solution. The organic phase was dried with sodium sulfate, filtered and the solvent was removed in vacuo. The residue was dissolved in 2N aqueous hydrochloric acid. The hydrochloric acid was removed in vacuo, the residue was dissolved in acetonitrile and added to water. This mixture was lyophilized. Yield 950 mg. MS (ES$^+$): m/e=594.4 (M+H)$^+$.

Example 32

(2S)-2-(Naphthalene-1-sulfonylamino)-3-(4-(2-(1,4,5,6-tetrahydropyrimidin-2-ylcarbamoyl)-ethyl)-benzoylamino)-propionic acid isobutyl ester

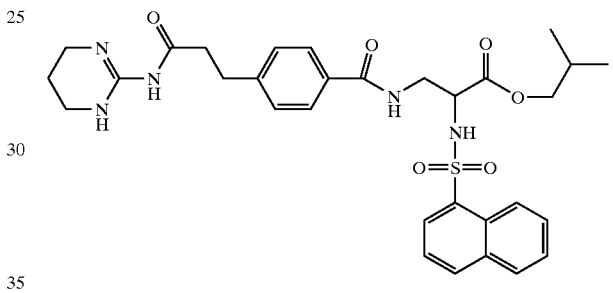

600 mg of (2S)-2-(naphthalene-1-sulfonylamino)-3-(4-(2-(1,4,5,6-tetrahydropyrimidin-2-ylcarbamoyl)-ethyl)-benzoylamino)-propionic acid was dissolved in 12 ml of isobutanol and 0.1 ml of concentrated sulfuric acid was added. The reaction solution was boiled for 24 hours. The solvent was removed in vacuo, and the residue was chromatographed on silica gel eluting with dichloromethane/methanol/acetic acid/water (9/1/0.1/0.1). The product was dissolved in acetic acid/water and lyophilized. Yield 250 mg. MS (ES$^+$): m/e=608.5 (M+H)$^+$.

Pharmacological Testing

The inhibition of bone resorption by the compounds according to the invention can be determined, for example, with the aid of an osteoclast resorption test ("PIT ASSAY"), for example analogously to WO-A-95/32710 which is incorporated herein by reference.

The inhibitory action of the compounds according to the invention against the vitronectin receptor $\alpha_v\beta_3$ can be determined, for example, as described below.

Test for the Measurement of the Inhibition of Binding of 293 Cells to Human Vitronectin (Vn/293 Cell Test)

1. Purification of Human Vitronectin

Human vitronectin is isolated from human plasma and purified by affinity chromatography according to the method of Yatohyo et al., *Cell Structure and Function* 23: 281–292 (1988).

2. Cell Test 293 cells, a human embryonic kidney cell line, which are cotransfected with DNA sequences for the $\alpha_v$ and $\beta_3$ subunits of the vitronectin receptor $\alpha_v\beta_3$, are selected for a high rate of expression (>500,000 $\alpha_v\beta_3$ receptors/cell) according to the FACS method. The selected cells are cultured and sorted again by means of FACS in order to obtain a stable cell line (15 D) with expression rates >1,000,000 copies of $\alpha_v\beta_3$ per cell.

A Linbro 96-well tissue culture plate with a flat bottom is coated overnight at 4° C. with human vitronectin (0.01 mg/ml, 0.05 ml/well) in phosphate-buffered saline solution (PBS) and then blocked with 0.5% strength BSA (bovine serum albumin). Solutions of the test substances from $10^{-10}$ mol/l to $2\times10^{-3}$ mol/l in glucose-containing DMEM medium are prepared and 0.05 ml/well of the solution are added to the plate in each case. The cells which express high levels of $\alpha_v\beta_3$ (for example 15 D) are suspended in glucose-containing DMEM medium and the suspension is adjusted to a content of 25,000 cells/0.05 ml of medium. 0.05 ml of this cell suspension is added to each well and the plate is incubated at 37° C. for 90 minutes. The plate is washed three times with warm PBS in order to remove unbound cells. The bound cells are lyzed in citrate buffer (25 mM, pH 5.0) which contains 0.25% Triton X-100. The hexoseamidase substrate p-nitrophenyl-N-acetyl-β-D-glucosaminide is then added and the plate is incubated at 37° C. for 90 minutes. The reaction is stopped with a glycine (50 mM)/EDTA (5 mM) buffer (ph 10.4), and the absorption of each well is measured at 405–650 nm. The data are analyzed according to standard processes.

The following test results (inhibitory concentrations $IC_{50}$) were obtained:

| Example Number | $IC_{50}$ Vn/293 cell test |
|---|---|
| 1 | 6 nM |
| 2 | 52 nM |
| 3 | 27 nM |
| 5 | 18 nM |
| 6 | 32 nM |
| 7 | 28 nM |
| 8 | 20 nM |
| 9 | 69 nM |
| 10 | 29 nM |
| 11 | 24 nM |
| 12 | 27 nM |
| 13 | 27 nM |
| 14 | 10 nM |
| 15 | 6 nM |
| 16 | 26 nM |
| 17 | 9 nM |
| 18 | 14 nM |
| 19 | 38 nM |
| 20 | 5 nM |
| 21 | 21 nM |
| 22 | 10 nM |
| 23 | 30 nM |
| 24 | 100 nM |

The invention described herein may be embodied in other specific forms without departing from the spirit or essential characteristics thereof. The specific embodiments previously described are therefore to be considered as illustrative of, and not limiting, the scope of the invention. Additionally, the disclosure of all publications and patent applications cited above, including United States Provisional Patent Application Serial No. 60/072,313, are expressly incorporated herein by reference in their entireties to the same extent as if each were incorporated by reference individually.

We claim:

1. A compound having the general formula II,

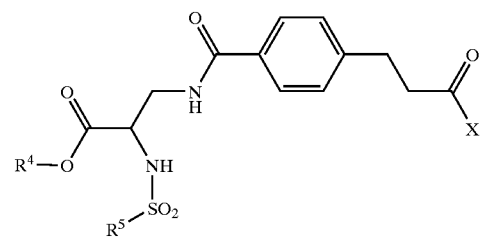

wherein:

$R^4$ is hydrogen, $(C_1-C_6)$-alkyl-CO—O—$(C_1-C_4)$-alkyl-, or $(C_1-C_6)$-alkyl, which is unsubstituted or is substituted by a radical selected from the group consisting of hydroxyl, $(C_1-C_4)$-alkoxy, $(C_1-C_4)$-alkyl-S(O)$_2$—, —NR$^7$R$^{7'}$, and —N$^+$R$^7$R$^{7'}$R$^{7''}$Q$^-$, where R$^7$, R$^{7'}$, and R$^{7''}$ independently of one another are hydrogen, $(C_1-C_6)$-alkyl, $(C_5-C_{14})$-aryl, or $(C_5-C_{14})$-aryl-$(C_1-C_6)$-alkyl- and Q$^-$ is a physiologically tolerable anion, or in which R$^4$ is one of the radicals

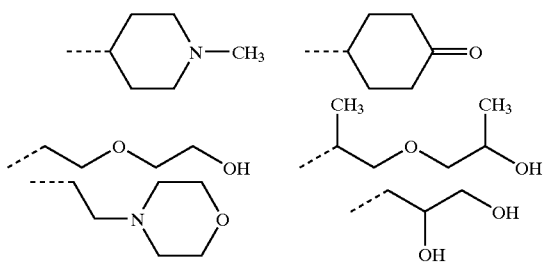

in which the bonds, via which the radicals are bonded, are indicated by dashed lines;

$R^5$ is $(C_1-C_{20})$-alkyl, $(C_3-C_{20})$-monocycloalkyl, $(C_5-C_{20})$-bicycloalkyl, $(C_5-C_{20})$-tricycloalkyl, $(C_6-C_{14})$-aryl, $(C_5-C_{14})$-heteroaryl, $(C_6-C_{14})$-aryl-$(C_1-C_6)$-alkyl- or $(C_5-C_{14})$-heteroaryl-$(C_1-C_6)$-alkyl-, wherein one or more carbon atoms of the alkyl radical, the monocycloalkyl radical, the bicycloalkyl radical, and the tricycloalkyl radical is optionally replaced by identical or different atoms selected from the group consisting of nitrogen, oxygen, and sulfur, and wherein the aryl radical, the heteroaryl radical, the alkyl radical, the monocycloalkyl radical, the bicycloalkyl radical, and the tricycloalkyl radical each is unsubstituted or is substituted by one, two, or three radicals $R^3$; and X is a nucleophilically substitutable leaving group;

in all their stereoisomeric forms and mixtures thereof in all ratios.

2. The compound of claim 1, wherein X is selected from the group consisting of hydroxyl, halogen, alkoxy, and aryloxy.

3. The compound of claim 2, wherein X is hydroxyl.

4. The compound of claim 1, wherein X is selected from the group consisting of chlorine, bromine, methoxy, ethyoxy, phenoxy, pentafluorophenoxy, phenylthio, methylthio, 2-pyridylthio, a radical of a nitrogen heterocycle bonded via a nitrogen atom.

5. The compound of claim 1, wherein X is selected from the group consisting of 1-imidazolyl, $((C_1-C_4)$-alkyl)-O—CO—O—, and tolylsulfonyloxy.

6. A process for the preparation of a compound having the general formula I,

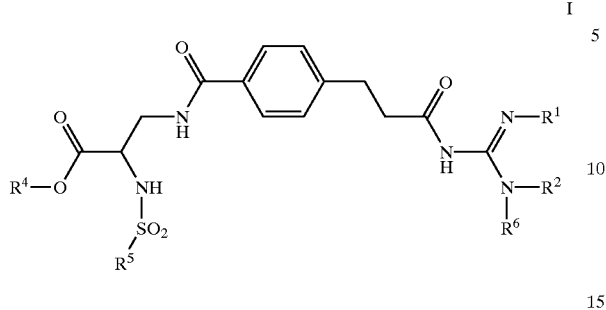

wherein:

- $R^1$ and $R^2$ independently of one another are hydrogen or $(C_1–C_6)$-alkyl which is unsubstituted or substituted by $R^3$, or in which the radicals $R^1$— and $R^2$— together are a saturated or unsaturated bivalent $(C_2–C_9)$-alkylene radical which is unsubstituted or is substituted by one or more groups from the group consisting of halogen, $(C_1–C_6)$-alkyl, $(C_1–C_6)$-alkoxy, $(C_6–C_{14})$-aryl, $(C_6–C_{14})$-aryl-$(C_1–C_6)$-alkyl-, $(C_5–C_{14})$-heteroaryl, $(C_5–C_{14})$-heteroaryl-$(C_1–C_6)$-alkyl-, $(C_3–C_{12})$-cycloalkyl, $(C_3–C_{12})$-cycloalkyl-$(C_1–C_6)$-alkyl- and oxo, where a 5-membered to 7-membered saturated or unsaturated ring which is unsubstituted or is substituted by $R^3$ and which is a carbocyclic ring or a heterocyclic ring containing one or two ring nitrogen atoms, can be fused to a carbon-carbon bond in the $(C_2–C_9)$-alkylene radical;
- $R^3$ is $(C_1–C_{10})$-alkyl, $(C_3–C_{20})$-monocycloalkyl, $(C_5–C_{20})$-bicycloalkyl, $(C_5–C_{20})$-tricycloalkyl, $(C_1–C_8)$-alkoxy, $(C_6–C_{14})$-aryl, $(C_6–C_{14})$-aryl-$(C_1–C_4)$-alkyl-, $(C_5–C_{14})$-heteroaryl, $(C_5–C_{14})$-heteroaryl-$(C_1–C_4)$-alkyl-, halogen, trifluoromethyl, cyano, hydroxyl, oxo, nitro, amino, —NR—$(C_1–C_4)$-alkyl, —N$((C_1–C_4)$-alkyl$)_2$, —NH—CO—$(C_1–C_4)$-alkyl, or —CO—$(C_1–C_4)$-alkyl;
- $R^4$ is hydrogen, $(C_1–C_6)$-alkyl-CO—O—$(C_1–C_4)$-alkyl- or $(C_1–C_6)$-alkyl which is unsubstituted or is substituted by a radical selected from the group consisting of hydroxyl, $(C_1–C_4)$-alkoxy, $(C_1–C_4)$-alkyl-S(O)$_2$—, —NR$^7$R$^{7'}$ and —N$^+$R$^7$R$^{7'}$R$^{7''}$Q$^-$, where R$^7$, R$^{7'}$ and R$^{7''}$ independently of one another are hydrogen, $(C_1–C_6)$-alkyl, $(C_5–C_{14})$-aryl or $(C_5–C_{14})$-aryl-$(C_1–C_6)$-alkyl- and Q$^-$ is a physiologically tolerable anion, or in which $R^4$ is one of the radicals

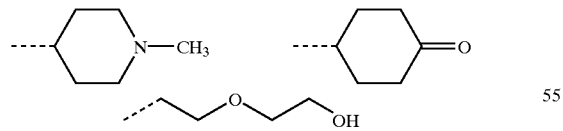

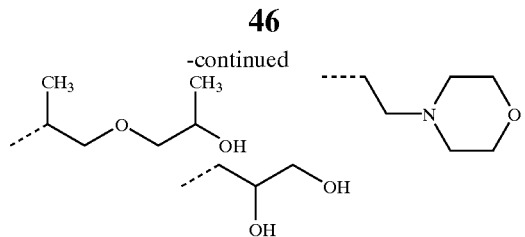

in which the bonds, via which the radicals are bonded, are indicated by dashed lines;

- $R^5$ is $(C_1–C_{20})$-alkyl, $(C_3–C_{20})$-monocycloalkyl, $(C_5–C_{20})$-bicycloalkyl, $(C_5–C_{20})$-tricycloalkyl, $(C_6–C_{14})$-aryl, $(C_5–C_{14})$-heteroaryl, $(C_6–C_{14})$-aryl-$(C_1–C_6)$-alkyl- or $(C_5–C_{14})$-heteroaryl-$(C_1–C_6)$-alkyl-, wherein one or more carbon atoms of the alkyl radical, the monocycloalkyl radical, the bicycloalkyl radical and the tricycloalkyl radical is optionally replaced by identical or different atoms selected from the group consisting of nitrogen, oxygen and sulfur, and wherein the aryl radical, the heteroaryl radical, the alkyl radical, the monocycloalkyl radical, the bicycloalkyl radical and the tricycloalkyl radical each is unsubstituted or is substituted by one, two or three radicals $R^3$; and
- $R^6$ is hydrogen, $(C_1–C_6)$-alkyl-O—CO—, hydroxyl, $(C_1–C_6)$-alkyl-O—CO—O— or nitro;

in all their stereoisomeric forms and mixtures thereof in all ratios, and their physiologically tolerable salts and their prodrugs, comprising linking two or more fragments which can be derived retrosynthetically from the compound of formula I, wherein the fragments are:

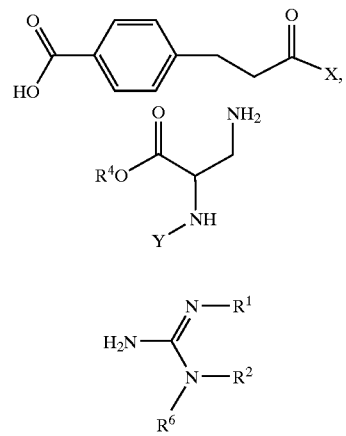

where Y is SO$_2$—R$^5$ and X is a nucleophilically substitutable leaving group.

* * * * *